(12) United States Patent
Mistretta

(10) Patent No.: US 7,545,901 B2
(45) Date of Patent: *Jun. 9, 2009

(54) BACKPROJECTION RECONSTRUCTION METHOD FOR CT IMAGING

(75) Inventor: Charles A. Mistretta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 271 days.

This patent is subject to a terminal disclaimer.

(21) Appl. No.: 11/482,858

(22) Filed: Jul. 7, 2006

(65) Prior Publication Data

US 2007/0009080 A1  Jan. 11, 2007

Related U.S. Application Data

(60) Provisional application No. 60/739,554, filed on Nov. 23, 2005, provisional application No. 60/716,865, filed on Sep. 14, 2005, provisional application No. 60/697,607, filed on Jul. 8, 2005.

(51) Int. Cl.
*A61B 6/03* (2006.01)

(52) U.S. Cl. .......................................... 378/4; 378/901

(58) Field of Classification Search .................... 378/4, 378/9, 210, 901
See application file for complete search history.

(56) References Cited

U.S. PATENT DOCUMENTS

| 5,502,385 | A | 3/1996 | Kuhn et al. |
| 5,603,322 | A | 2/1997 | Jesmanowicz et al. |
| 5,604,775 | A | 2/1997 | Saitoh et al. |
| 5,604,778 | A | 2/1997 | Polacin et al. |
| 5,933,006 | A | 8/1999 | Rasche et al. |
| 6,275,560 | B1 * | 8/2001 | Blake et al. .................... 378/8 |
| 6,487,435 | B2 | 11/2002 | Mistretta et al. |
| 6,490,472 | B1 | 12/2002 | Li et al. |
| 6,710,686 | B2 | 3/2004 | Mertelmeier et al. |

(Continued)

FOREIGN PATENT DOCUMENTS

EP    0 627 633 A1    7/1994

(Continued)

OTHER PUBLICATIONS

Badea et al., Experiments with the nonlinear and chaotic behaviour of the multiplicative algebraic reconstruction technique (MART) algorithm for computed tomography, Mar. 24, 2004, Physics in Medicine and Biology, vol. 49, pp. 1455-1474.*

(Continued)

*Primary Examiner*—Edward J Glick
*Assistant Examiner*—John M Corbett
(74) *Attorney, Agent, or Firm*—Quarles & Brady LLP

(57) ABSTRACT

Two-dimensional or three-dimensional, time-resolved CT frame images are acquired during a dynamic study of a subject. A composite image is produced and this is used to reconstruct each CT frame image by weighting the backprojection of each projection view acquired for that image frame by the corresponding value in the composite image. This weighted backprojection enables artifact-free image frames to be produced with far fewer projection views of the subject. The composite image may be reconstructed from views acquired separately, or it may be produced by combining views acquired during the course of the dynamic study.

35 Claims, 15 Drawing Sheets

U.S. PATENT DOCUMENTS

| | | | |
|---|---|---|---|
| 6,807,248 B2 | 10/2004 | Mihara et al. | |
| 6,954,067 B2 | 10/2005 | Mistretta | |
| 7,324,623 B2 * | 1/2008 | Heuscher | 378/9 |
| 2001/0027262 A1 | 10/2001 | Mistretta et al. | |
| 2003/0013953 A1* | 1/2003 | Mistretta | 600/425 |
| 2003/0190065 A1* | 10/2003 | Hamill et al. | 382/131 |
| 2004/0136490 A1* | 7/2004 | Edic et al. | 378/4 |

FOREIGN PATENT DOCUMENTS

| | | |
|---|---|---|
| WO | WO03/051201 A2 * | 6/2003 |
| WO | WO 2005/026765 | 3/2005 |
| WO | WO 2005/069031 | 7/2005 |

OTHER PUBLICATIONS

Y. Huang et al, Time-Resolved 3D MR Angiography by Interleaved Biplane Projection, Proc. Intl. Soc. Mag. Reson. Med. 13 (2005).

T.A. Cashen et al, Comparison of Temporal and Spatial Undersampling Techniques for Time-Resolved Contrast-Enhanced MR Angiography, Proc. Intl. Soc. Mag. Reson. Med. 13, (2005).

Graeme C. McKinnon et al, Towards Imaging the Beating Heart Usefully with a Conventional CT Scanner, Trans. on Biomedical Eng., vol. BME-28, No. 2, p. 123-127, Feb. 1981.

Kathryn L. Garden et al, 3-D Reconstruction of the Heart from few Projections: A Practical Implementation of the McKinnon-Bates Algorithm, Trans. on Biomedical Eng., vol. MI-5, No. 4, p. 233-234, Dec. 1986.

C.A. Mistretta et al, Highly Constrained Backprojection for Time-Resolved MRI, Mag. Reson. Med. 55:30-40 (2006).

Zhi-Pei Liang et al, Constrained Reconstruction Methods in MR Imaging, Reviews of Mag. Reson. in Med. vol. 4, pp. 67-185, 1992.

J.G. Pipe et al, Spiral Projection Imaging: a new fast 3D trajectory, Proc. Intl. Soc. Mag. Reson. Med. 13, (2005).

K.V. Koladia et al, Rapid 3D PC-MRA using Spiral Projection Imaging, Proc. Intl. Soc. Mag. Reson. Med. 13, (2005).

J. Tsao et al, k-t BLAST and k-t SENSE: Dynamic MRI With High Frame Rate Exploiting Spatiotemporal Correlations, Mag. Reson. Med. 50:1031-1042 (2003).

Zhi-Pei Liang et al, Constrained Imaging-Overcoming the Limitations for the Fourier Series, IEEE Engineering in Medicine and Biology, Sep./Oct. 1996, pp. 126-132.

Zhi-Pei Liang et al, Fast Algorithm for GS-Model-Based Image Reconstruction in Data-Sharing Fourier Imaging, IEEE Transactions on Med. Imaging, vol. 22, No. 8, pp. 1026-1030, Aug. 2003.

Klass P. Pruessmann et al, Advances in Sensitivity Encoding With Arbitrary k-Space Trajectories, Mag. Reson. in Med. 46:638-651 (2001).

R. Fahrig et al, Use of a C-Arm System to Generate True Three-dimensional Computed Rotational Angiograms: Preliminary In Vitro and In Vivo Results, AJNR: 18, pp. 1507-1514,Sep. 1997.

A.V. Barger, et al, Single Breath-Hold 3D Contrast-Enhanced Method for Assessment of Cardiac Function, Mag. Reson. in Med. 44:821-824 (2000).

J. Du et al, Time-Resolved Undersampled Projection Reconstruction Imaging for High-Resolution CE-MRA of the Distal Runoff Vessels, Mag. Reson. in Med. 48:516-522 (2002).

Xavier Golay, et al, Presto-Sense: An Ultrafast Whole-Brain fMRI Technique, Mag. Reson. in Med. 43:779-786 (2000).

Ronald R. Price, et al, Practical Aspects of Functional MRI (NMR Task Group #6), Medical Physics, vol. 29, No. 8, pp. 1892-1912, Aug. 2002.

M.S. Hansen et al, k-t Blast Reconstruction From Arbitrary k-t space Sampling: Application To Dynamic Radial Imaging, Prob. Intl. Soc. Mag. Reson. Med. 13 p. 684 (2005).

Schmidlin, P., Subsets and Overrelaxation in Iterative Image Reconstruction, Phys. Med. Biol. 44 (1999), 1385-1396.

Fahrig, Lownie and Holdsworth (Use of a C-Arm system to generate True 3D Computed Tomography Rotational Angiograms; Preliminary in vitro and In vivo Results. R. Fahrig, S. Lownie, and DW Holdsworth, AJNR 18:1507-154, Sep. 1997).

R. Boubertakh et al., Dynamic Images Reconstruction using kt-Blast without Training Data, Proc. Intl. Soc. Med. 11 p. 343 (2004).

P. Irarrazaval et al., Reconstruction of Undersampled Dynamic Images Based on Time Frame Registration, Proc. Intl. Soc. Med. 11 p. 342 (2004).

J. Tsao et al., Optimized canonical sampling patterns in k-t space with two and three spatial dimensions for k-t BLAST and k-t$^1$, Proc. Intl. Soc. Med. 11 p. 261 (2004).

M.S. Hansen et al., A study of the spatial-temporal tradeoff in k-t BLAST reconstruction, Proc. Intl. Soc. Med. 11 p. 536 (2004).

J. Tsao et al., Moving-buffer k-t BLAST for real-time reconstruction: Cartesian & simplified radial cases, Proc. Intl. Soc. Med. 11 p. 635 (2004).

F. Huang et al., Reconstruction with Prior Information for Dynamic MRI, Proc. Intl. Soc. Med. 11 p. 2680 (2004).

D. Mitsouras et al., Accelerated MR Imaging via FOLDing the non-Fourier Encoded Dimensions, Proc. Intl. Soc. Med. 11 p. 2092 (2004).

P.C. Lauterbur and Z. Liang, Magnetic Resonance Imaging with a priori Constraints: Possibilities and Limitations, IEEE Engineering in Medicine and Biology Society, 1996.

C. Baltes et al., Considerations on training data in k-t BLAST / k-t SENSE accelerated quantitative flow measurements, Proc. Intl. Soc. Mag. Reson. Med. 13 p. 383 (2005).

M.S. Hansen et al., On the Influence of Training Data Quality in k-t BLAST Reconstruction, Mag. Reson. Med. 52:1175-1183 (2004).

M. Lustig et al., k-t SPARSE: High Frame Rate Dynamic MRI Exploiting Spatio-Temporal Sparsity, Proc. Intl. Soc. Mag. Reson. Med. 14 (2006).

J. Tsao et al., Unifying Linear Prior-Information-Driven Methods for Accelerated Image Acquisition, Mag. Reson. Med. 46:652-660 (2001).

Q. Xiang and R.M. Henkelman, K-Space Description for MR Imaing of Dynamic Objects, Mag. Reson. Med. 29:422-428 (1993).

M. Lustig et al., Rapid MR Imaging with Compressed Sensing and Randomly Under-Sampled 3DFT Trajectories, Proc. Intl. Soc. Mag. Reson. Med. 14 (2006).

S. Krishnan and T.L. Chenevert, Spatio-Temporal Bandwidth-Based Acquisition for Dynamic Contrast-Enhanced Magnetic Resonance Imaging, J. Mag. Reson. Imaging 20:129-137 (2004).

M.S. Hansen et al., k-t BLAST Reconstruction From Non-Cartesian k-t Space Sampling, Mag. Reson. Med. 55:85-91 (2006).

A.G. Webb et al., Application of Reduced-Encoding MR Imaging with Generalized-Series Reconstruction (RIGR), J. Mag. Reson. Imaging 3:925-928 (1993).

B. Madore and N.J. Pelc, New Approach to 3D Time-Resolved Angiography, Mag. Reson. Med. 47:1022-1025 (2002).

J. Tsao et al., Optimizing Spatiotemporal Sampling for k-t BLAST and k-t SENSE: Application to High-Resolution Real-Time Cardiac Steady-State Free Precession, Mag. Reson. Med. 53:1372-1382 (2005).

Schmidlin P et al.: "Subsets and overrelaxation in iterative image reconstruction" Physics in Medicine and Biology IOP Publishing UK, vol. 44, No. 5, May 1999, pp. 1385-1396, XP002405666 ISSN: 0031-9155.

Launay et al.: "3D reconstruction of cerebral vessels and pathologies from a few biplane digital angiographies" Visualization in Biomedical Computing. 4th International Conference, VBC '96 Proceedings Springer-Verlag Berlin, Germany, 1996, pp. 123-128, XP001247778, ISBN: 3-540-61649-7.

A.L. Wentland et al.: "Technique for acquiring MR images of CSF flow during a valsalva maneuver." Procs. of the 14th Scientific Meeting & Exhibition of the International Society for Magnetic Resonance in Medicine, Seattle, WA, USA, May 6-12, 2006, 1525.

K.M. Johnson et al., "Average and Time-Resolved Dual Velocity Encoded Phase Contrast Vastly Undersampled Isotropic Projection Imaging." ISMRM 2006, Seattle, WA, May 6-12, 2006.

K. M. Johnson et al., "Transtenotic Pressure Gradient Measurements Using Phase Contrast Vastly Undersampled Projection Imaging (PC-VIPR) in a Canine Model." ISMRM 2006, Seattle, WA, May 6-12, 2006.

Ashwani Aggarwal et al., "Imaging in Turbid Media by Modified Filtered Back Projection Method Using Data From Monte Carlo Simulation." Procs. Of SPIE 5047, pp. 314-324, Jul. 2003.

Weislaw L. Nowinski, The Iterated Normalized Backprojection Method of Image Reconstruction, Institute of Computer Science, Polish Academy of Sciences Ordona 21, 01-237 Warsaw, Poland, 1993.

* cited by examiner

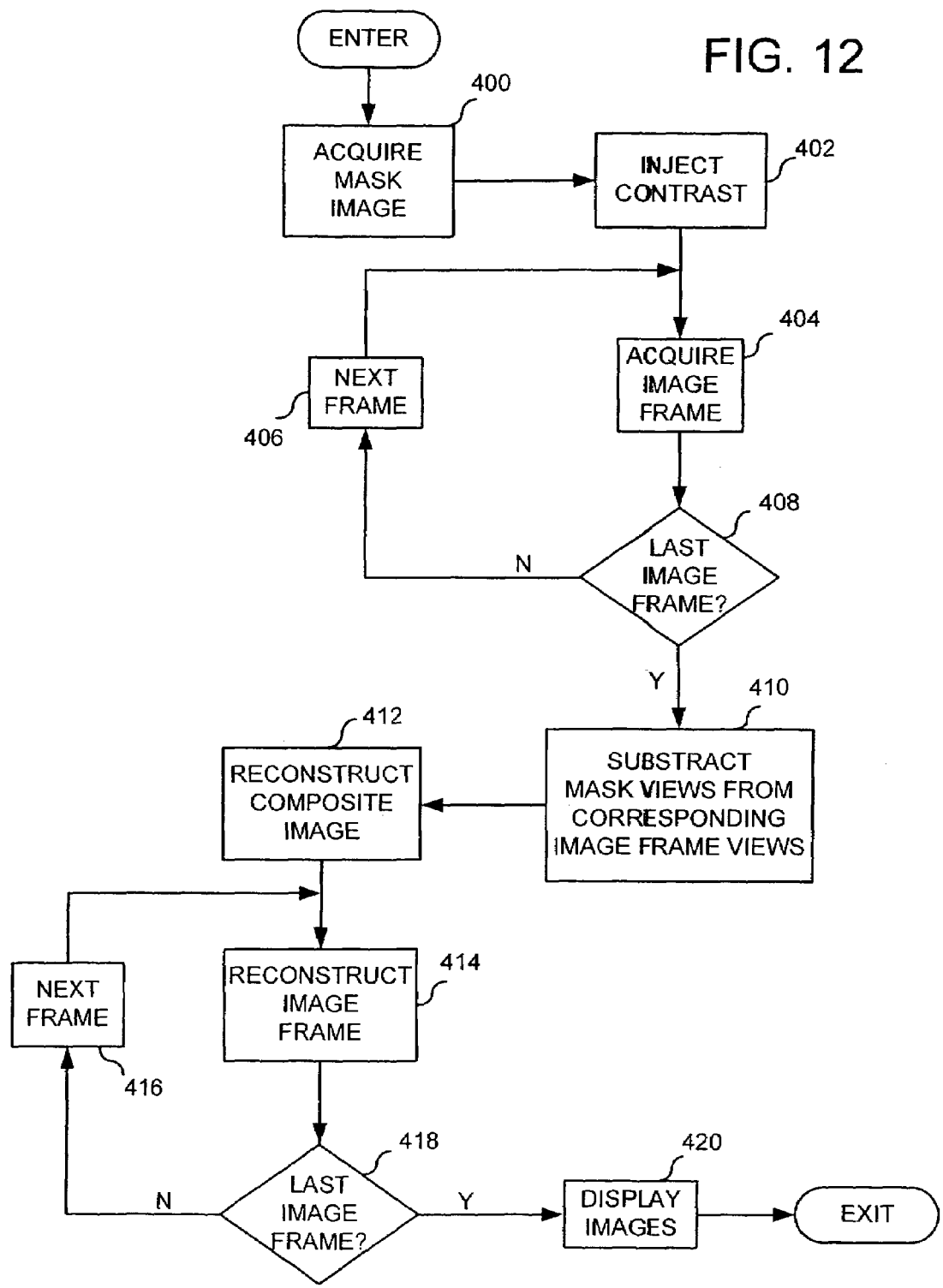

BACKPROJECTION RECONSTRUCTION METHOD FOR CT IMAGING

CROSS-REFERENCE TO RELATED APPLICATIONS

This application is based on U.S. Provisional Patent Application Ser. No. 60/697,607 filed on Jul. 8, 2005 and entitled "BACKPROJECTION RECONSTRUCTION METHOD FOR UNDERSAMPLED TIME-RESOLVED MR IMAGING", U.S. Provisional Pat. Appln. Ser. No. 60/716,865 filed on Sep. 14, 2005 and entitled "Backprojection Reconstruction Method For CT Imaging"; and U.S. Provisional Patent Application Ser. No. 60/739,554 filed on Nov. 23, 2005 and entitled "Backprojection Reconstruction Method For Low Dose CT Imaging".

STATEMENT REGARDING FEDERALLY SPONSORED RESEARCH

This invention was made with government support under Grant No. HL072260 awarded by the National Institute of Health. The United States Government has certain rights in this invention.

BACKGROUND OF THE INVENTION

The present invention relates to computed tomography, and more particularly, to a method and apparatus for reconstructing an image from projection data acquired using a computed tomography ("CT") system.

In a computed tomography system, an x-ray source projects a fan-shaped beam which is collimated to lie within an X-Y plane of a Cartesian coordinate system, termed the "image plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce what is called the "transmission profile," or "attenuation profile" or "projection."

The source and detector array in a conventional CT system are rotated on a gantry within the imaging plane and around the object so that the angle at which the x-ray beam intersects the object constantly changes. The transmission profile from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This image reconstruction process converts the attenuation measurements acquired during a scan into integers called "CT numbers" or "Hounsfield units", which are used to control the brightness of a corresponding pixel on a display.

The filtered backprojection image reconstruction method is the most common technique used to reconstruct CT images from acquired transmission profiles. As shown in FIG. 5 each acquired x-ray transmission profile 100 is backprojected onto the field of view (FOV) 102 by projecting each ray sum 104 in the profile 100 through the FOV 102 along the same ray path that produced the ray sum 104 as indicated by arrows 106. In projecting each ray sum 104 in the FOV 102 we have no a priori knowledge of the subject and the assumption is made that the x-ray attenuation in the FOV 102 is homogeneous and that the ray sum should be distributed equally in each pixel through which the ray path passes. For example, a ray path 108 is illustrated in FIG. 5 for a single ray sum 104 in one transmission profile 100 and it passes through N pixels in the FOV 102. The attenuation value (P) of this ray sum 104 is divided up equally between these N pixels:

$$\mu_n = (P \times 1)/N \tag{1}$$

where: $\mu_n$ is the attenuation value distributed to the $n^{th}$ pixel in a ray path having N pixels.

Clearly, the assumption that attenuation in the FOV 102 is homogeneous is not correct. However, as is well known in the art, if certain corrections are made to each transmission profile 100 and a sufficient number of profiles are acquired at a corresponding number of projection angles, the errors caused by this faulty assumption are minimized and image artifacts are suppressed. In a typical filtered backprojection method of image reconstruction, anywhere from 400 to 1000 views are typically required to adequately suppress image artifacts in a 2D CT image.

There are a number of clinical applications where the time required to acquire a large number of views is not available. In time-resolved angiography, for example, a series of images are acquired as contrast agent flows into the region of interest. Each image is acquired as rapidly as possible to obtain a series of snapshots that depicts the in flow of contrast. This application is particularly challenging when imaging coronary arteries or other vessels that require cardiac gating to suppress motion artifacts.

In Computer Rotation Angiography (CRA), a computed rotational angiography system such as that described by Fahrig, Lownie and Holdsworth (*Use of a C-Arm system to generate True 3D Computed Tomography Rotational Angiograms; Preliminary in vitro and In vivo Results*. R. Fahrig, S. Lownie, and D W Holdsworth, AJNR 18:1507-154, September 1997) is employed to acquire a series of three dimensional images during the uptake of a contrast agent. Because it is desirable to acquire the three-dimensional data sets obtained using this apparatus as quickly as possible in order to provide a high time resolution during the dynamic study, only 120 projection angles, or views, are acquired for each image. This is significantly less than that demanded by the Nyquist sampling theorem. Therefore, the angiogram reconstructed from a single data set contains streak artifacts. These streak artifacts preclude the use of this CRA method for intravenous angiography because of the reduced vasculature contrast provided by this contrast injection method.

Another issue with x-ray CT is the x-ray dose to which the subject is exposed during the scan. To obtain a higher resolution and artifact free image it is necessary to obtain many views at a high enough x-ray beam intensity to reconstruct an image at the desired signal-to-noise ratio (SNR). The dose level may be reduced by decreasing the beam strength or reducing the number of acquired views, but either step also reduces the SNR of the reconstructed image.

SUMMARY OF THE INVENTION

The present invention is a new method for reconstructing CT images, and particularly, an improved backprojection method. A composite image is acquired and reconstructed to provide a priori knowledge of the subject being imaged. This composite image is used during the backprojection of acquired images to weight the distribution of the back projected attenuation data. As a result, quality CT images can be reconstructed using fewer projection views of the subject, or using projection views acquired with a lower x-ray dose.

A discovery of the present invention is that good quality CT images can be produced with far fewer attenuation profiles if a priori knowledge of the x-ray attenuation contour in the FOV 102 is used in the backprojection process instead of the assumed homogeneous attenuation contour. Referring to FIG. 6, for example, the attenuation contour in the FOV 102 may be known to include structures such as blood vessels 110 and 112. That being the case, when the backprojection ray path 108 passes through these structures a more accurate distribution of the ray sum 104 in each ray path pixel is achieved by weighting the distribution as a function of the known attenuation contour at that pixel location. As a result, a majority of the ray sum 104 will be distributed in the example of FIG. 6 at the ray path pixels that intersect the structures 110 and 112. For a backprojection ray path 108 having N pixels this may be expressed as follows:

$$\mu_n = (P \times C_n) / \sum_{n=1}^{N} C_n \qquad (2)$$

where: P=the ray sum attenuation value; and
$C_n$=attenuation value of an a priori composite image at the $n^{th}$ pixel along the backprojection ray path.

The numerator in equation (2) weights each pixel using the corresponding attenuation value in the composite image and the denominator normalizes the value so that all back-projected ray sums are given equal weight by the process.

It should be noted that while the normalization can be performed on each pixel separately after the backprojection, in many clinical applications it is far easier to normalize the ray sum attenuation value P before the backprojection. In this case, the ray sum P is normalized by dividing by the corresponding value $P_c$ in a projection through the composite image at the same view angle. The normalized ray sum $P/P_c$ for each view angle is backprojected and summed to form an unconstrained image, and the resulting unconstrained image is then multiplied by the composite image.

A 3D embodiment of the highly constrained backprojection is shown pictorially in FIG. 14 for a single 3D projection view characterized by the view angles θ and φ. This projection view is back projected along axis 116 and spread into a Radon plane 121 at a distance r along the back projection axis 116. Instead of a filtered back projection in which projection signal values are filtered and uniformly distributed into the successive Radon planes, along axis 116, the projection signal values are distributed in the Radon plane 121 using the information in the composite image. The composite image in the example of FIG. 14 contains vessels 118 and 120. The weighted attenuation value is deposited at image location x, y, z in the Radon plane 121 based on the value at the corresponding location x, y, z in the composite image. This is a simple multiplication of the backprojected ray sum value P by the corresponding composite image pixel value. This product is then normalized by dividing the product by the ray sum attenuation value from the corresponding image space projection view of the composite image. The formula for the 3D reconstruction is $$I(x,y,z) = \Sigma(P(r,\theta,\phi) * C(x,y,z)_{(r,\theta,\phi)}/P_c(r,\theta,\phi)) \qquad (2a)$$

where the sum (Σ) is over all projections in the image frame being reconstructed and the x, y, z values in a particular Radon plane are calculated using the projection ray sum value P(r, θ, φ) at the appropriate r, θ, φ value for that plane. $P_c(r,\theta,\phi)$ is the corresponding ray sum attenuation value from the composite image, and $C(x,y,z)_{(r,\theta,\phi)}$ is the composite image value at (r, θ, φ).

Another discovery of the present invention is that there are a number of clinical CT applications in which a priori information is available and a composite image can be reconstructed and used to enhance the reconstruction of images. When a series of time-resolved images are acquired in a dynamic study, each image frame may be reconstructed using a very limited set of acquired views in order to increase the time resolution of the study. To employ the highly constrained backprojection reconstruction method of the present invention, each such set of image frame views is interleaved with the views acquired for other image frames. After a number of image frames have been acquired, a sufficient number of different, interleaved views are available to reconstruct a quality composite image.

Another objective of the present invention is to enable an image to be acquired with a lower x-ray dose without significant loss of image SNR. By using a high SNR composite image in the highly constrained backprojection method of the present invention, the SNR of an image frame reconstructed from a lower dose set of projection views is significantly increased; For example, in a perfusion study in which contrast agent flowing into tissues is repeatedly imaged, a high SNR composite image may be acquired and a series of low dose image frames may be acquired during the study. By using the high SNR composite image to reconstruct each image frame, the SNR of each image frame is substantially increased.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 12 is a flow chart of yet another preferred method for practicing the present invention;

DETAILED DESCRIPTION OF THE PREFERRED EMBODIMENT

Figure 1:
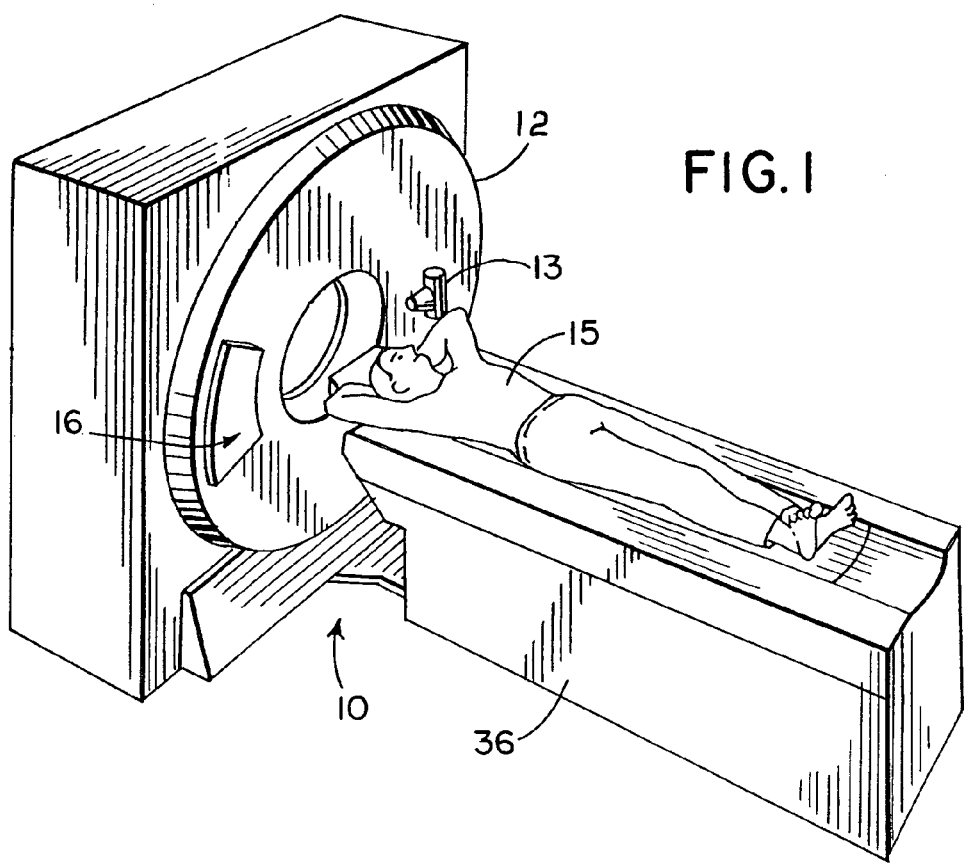
FIG. 1 is a perspective view of a first type of CT apparatus which can be used to practice the present invention.
Figure 2:
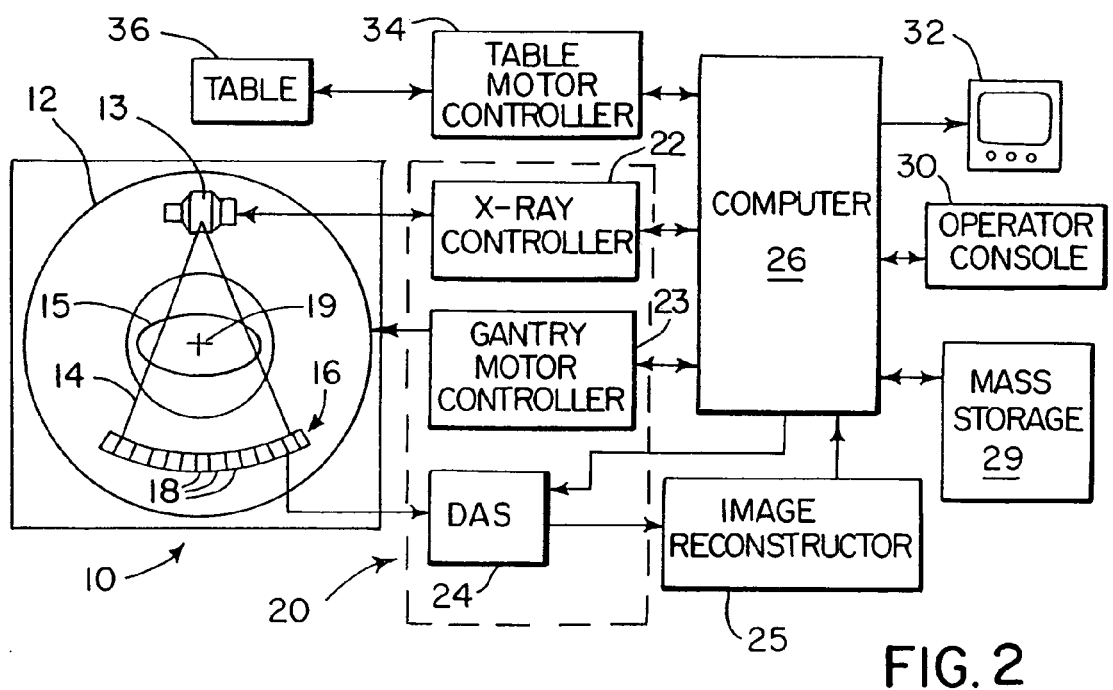
FIG. 2 is a block diagram of CT control system which can be used to control the CT apparatus of FIG. 1.

With initial reference to FIGS. 1 and 2, a computed tomography (CT) imaging system 10 includes a gantry 12 representative of a "third generation" CT scanner. Gantry 12 has an x-ray source 13 that projects a fan beam or a cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction according to the method of the present invention. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

Figure 3:
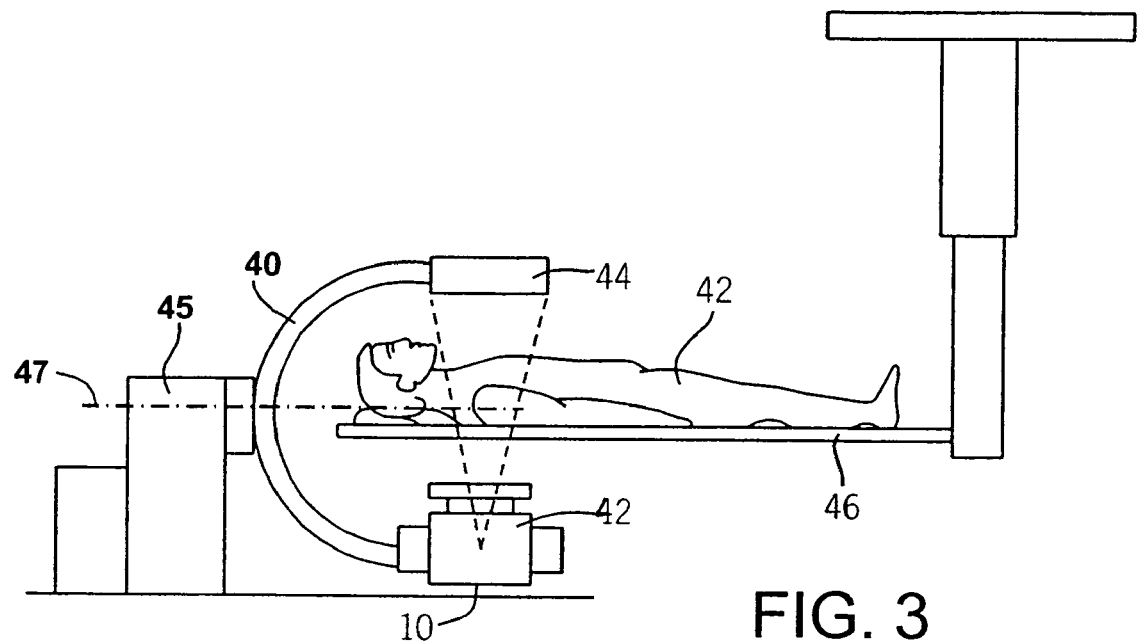
FIG. 3 is a perspective view of a second type of CT apparatus that can be used to practice the present invention.

Referring to FIG. 3, a second embodiment of a CT scanner which may employ the present invention comprises a C-arm 40 to which the two-dimensional detector 44 and X-ray source 42 are mounted. Here, again the patient 42 is positioned on a table 46. The C-arm 40 is rotationally mounted to a base 45, and data for the generation of three-dimensional images is obtained by rotating the X-ray source 42 and detector 44 around a defined axis 47. CT scanners of the type shown in FIG. 3 are particularly useful in angiography, as described in *Use of a C-Arm system to generate True 3D Computed Tomography Rotational Angiograms; Preliminary in vitro and In vivo Results*. R. Fahrig, S. Lownie, and D W Holdsworth, AJNR 18:1507-154, September 1997.

In the above described CT system a single x-ray source is revolved around the subject during a scan and the time resolution of each acquired image frame is limited by the time required to rotate the gantry through a substantial angle. This is necessary when an under-sampled data set is acquired in order for the acquired projection views to be evenly spaced and span the full angular range. It has been found that when the acquired projection views in an under sampled data set are evenly spaced, the point spread function is very good and artifacts only start to occur at some distance from the center of the FOV.

Figure 7:
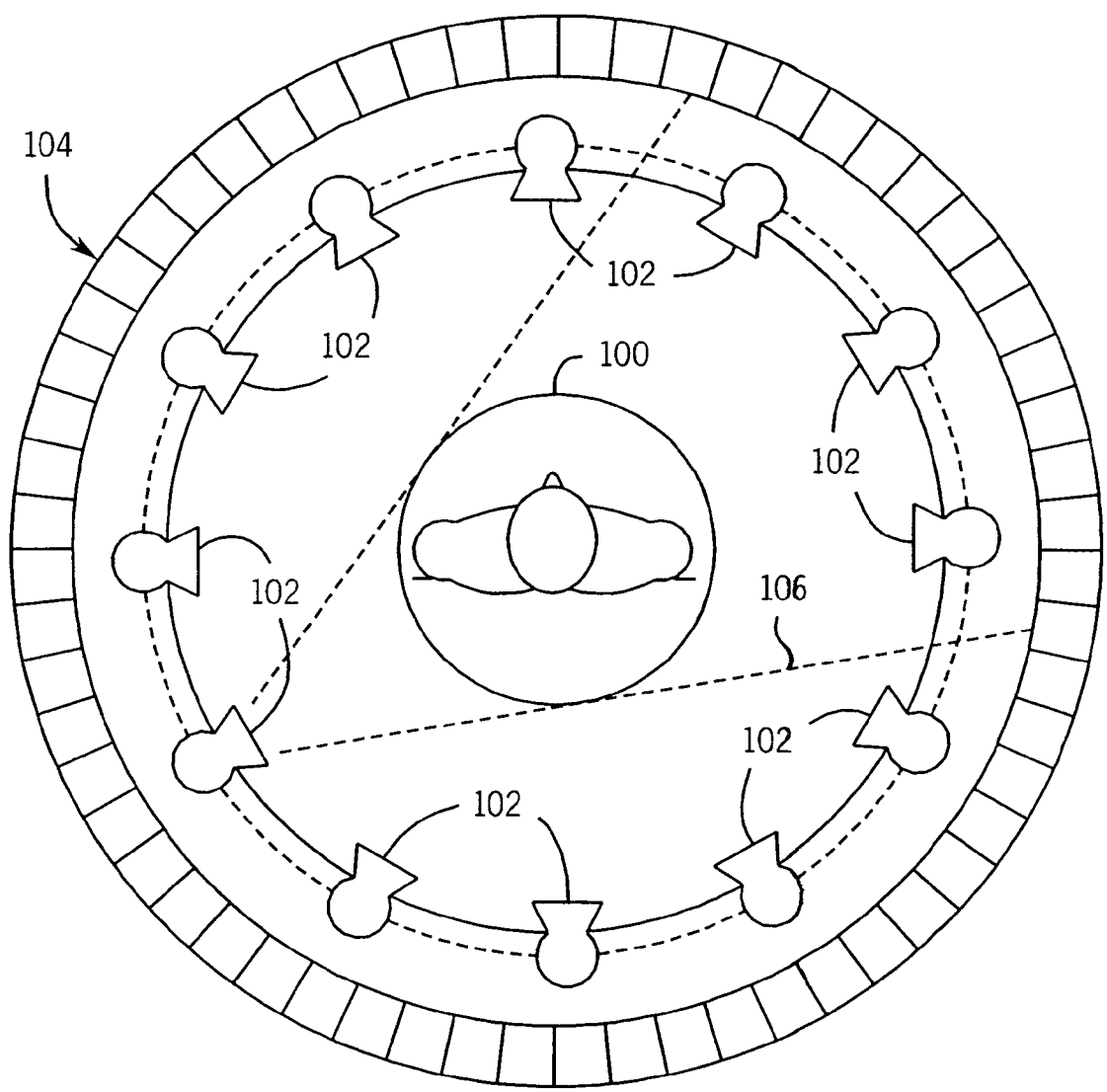
FIG. 7 is a pictorial representation of a third type of CT apparatus which can be used to practice the present invention.

To achieve very high time resolution during a dynamic study it is necessary to acquire each set of equally spaced projection views in a very short time frame. This is accomplished with the CT system shown in FIG. 7. Rather than moving a single x-ray source around an FOV 100, a set of separate x-ray sources 102 are disposed evenly around the FOV 100. A stationary 2D detector ring 104 is also disposed around the FOV 100 and sectors thereof receive and measure one projection view produced by an x-ray source 102 on the opposite side of the FOV 100 as indicated by dashed lines 106 for one source 102. Systems such as the Mayo Clinic Dynamic Spatial Reconstruction described by Robb, R. A., E. A. Hoffman, L. J. Sinak, L. D. Harris and E. L. Ritman: "High-Speed Three-Dimensional X-ray Computed Tomography: The Dynamic Spatial Reconstructor" Proceedings of the IEEE 71: 308-319 (march) 1983, may be used for this purpose.

One image frame is acquired with this CT system by energizing each x-ray source 102 in sequence for 0.5 msec and reading the attenuation profile from the detector 104. A complete image frame requires only 8 msec to acquire and then the ring of x-ray sources 102 is rotated a small angle to acquire the next frame of interleaved projection profiles.

Scanners such as those described above may be employed to produce time resolved angiograms during a contrast enhanced dynamic study of the subject. Initial rotations are performed to acquire a pre-injection mask which can be used to remove the effects of bones and artifacts from successively acquired images. After the pre-injection mask data is obtained, a contrast agent, preferably iodine, is injected. The iodine can be injected through typical arterial injection, but is preferably introduced intravenously, thereby reducing the invasiveness and discomfort of the procedure for the patient. Next, a time series of computed tomographic angiography (CTA) images are obtained to image the selected region of interest in the body. Rather than precisely timing the arrival of contrast into the vasculature being imaged, the strategy of a CTA dynamic study is to acquire a series of image frames during administration of the contrast agent. The physician is then able to select which image in the series best depicts the vasculature of interest. In addition to image quality and resolution, an important criteria in a CTA dynamic study is the rate at which images can be acquired. This is referred to as time resolution, and studies with higher time resolution increase the probability that an image with peak contrast in the vasculature of interest will be acquired.

Figure 4:
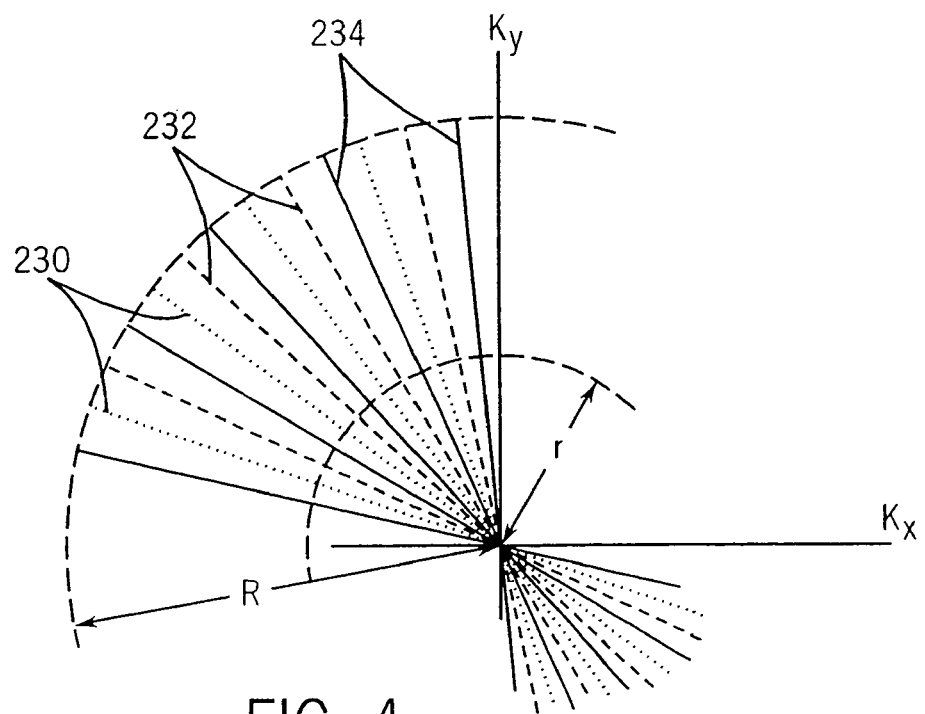
FIG. 4 is a graphic illustration of the interleaved acquisition of projection views in successive image frames.
Figure 5:
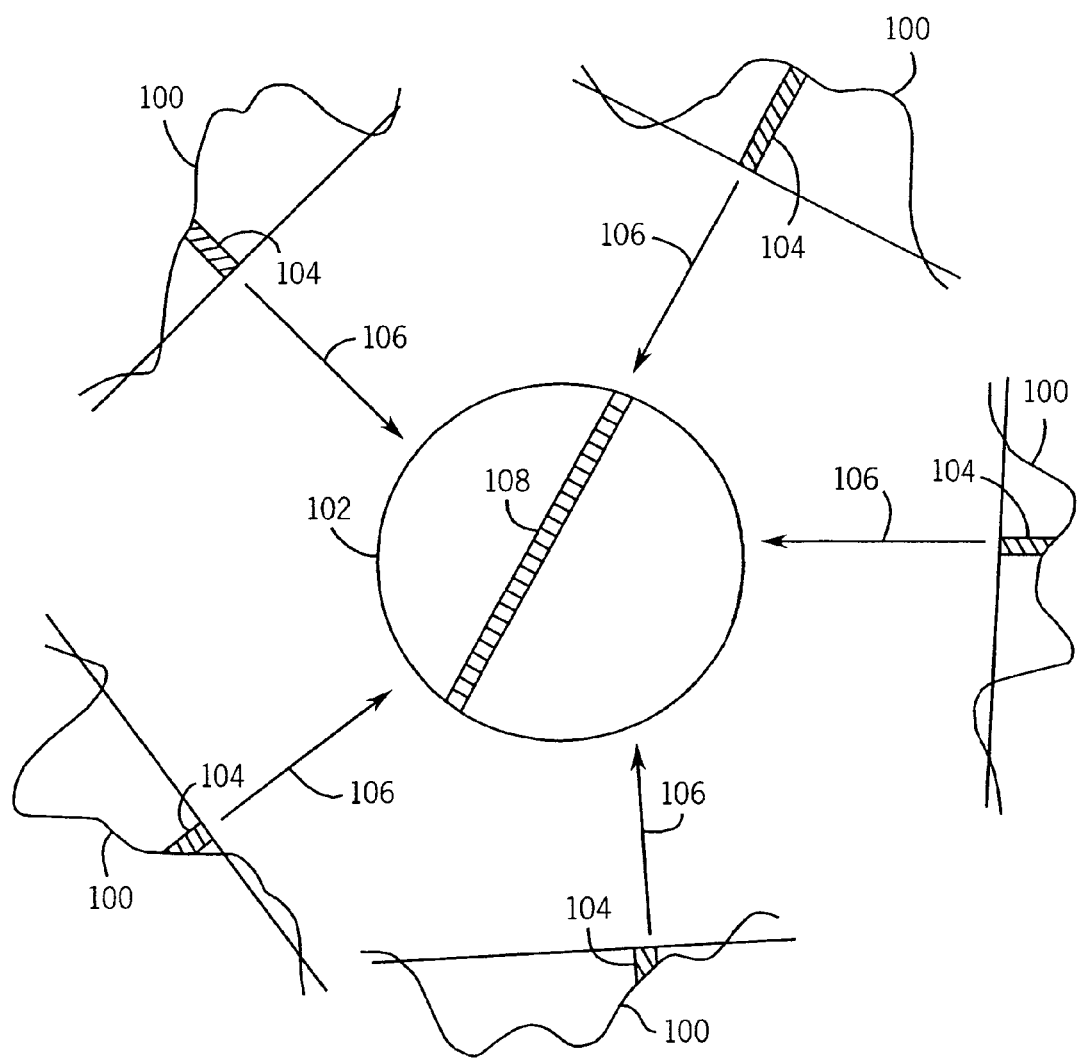
FIG. 5 is a pictorial representation of a conventional back-projection image reconstruction method.
Figure 6:
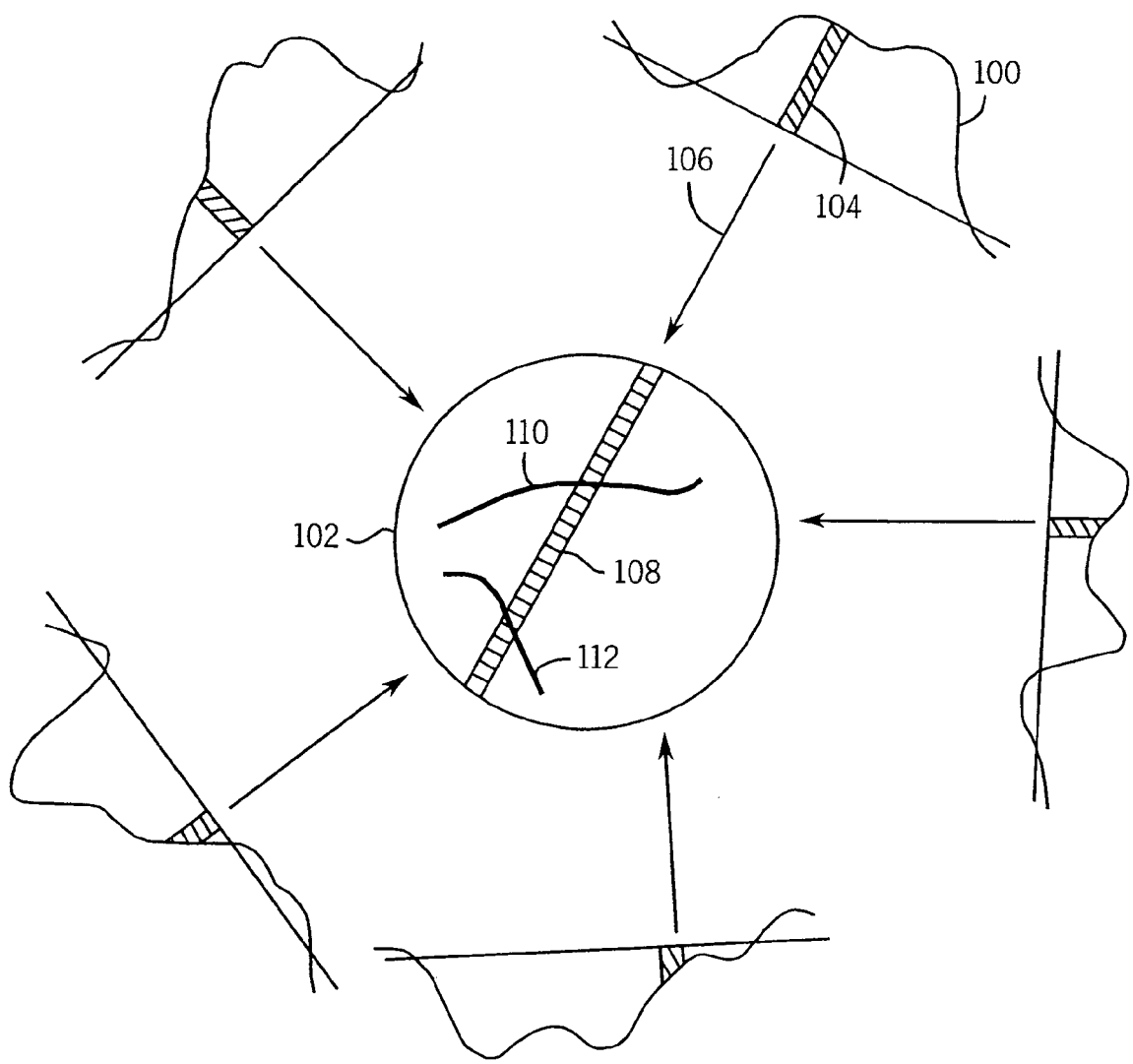
FIG. 6 is a pictorial representation of the highly constrained backprojection image reconstruction method according to the present invention.

The temporal resolution is increased by reducing the number of projections acquired for each image frame in the CTA dynamic study. If the projections acquired for each image frame are interleaved with the projections acquired for other image frames, a good quality composite image can be reconstructed by combining projections. Referring to FIG. 4 for example, if M projections are required to fully sample a k-space volume having a radius R, these M projections may be divided into sets of interleaved, equally spaced projection views and each set used to acquire an image frame. The sampling trajectories of the first set of projection views may be indicated, for example, by dotted lines 230, the second set is indicated by dashed lines 232, the third set by lines 234 and so on for as many image data sets as required until M interleaved projections are acquired. The M acquired projections fully sample k-space to the radius R and are used to reconstruct a quality composite image. This composite image is then used to reconstruct time resolved image frames from the respective sets of interleaved projection views using the highly constrained backprojection method of the present invention.

The same procedure may also be used when the objective is to lower the x-ray dose. Each image frame is acquired with fewer projection views and hence with a lower x-ray dose. The loss in image SNR that would otherwise occur is avoided by the highly constrained backprojection which conveys SNR from the high SNR composite image.

Figure 8:
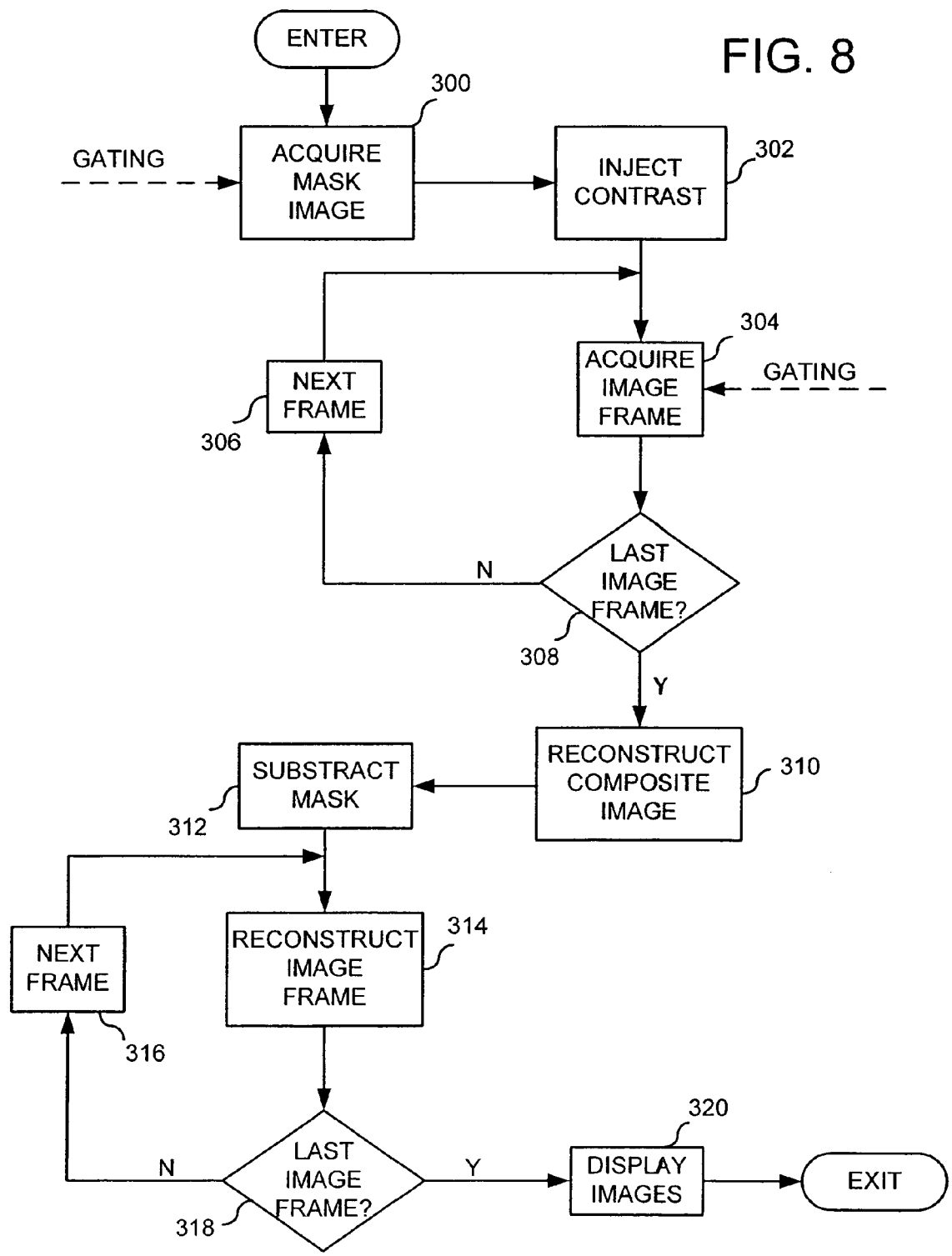
FIG. 8 is a flow cart of one preferred method for practicing the present invention.

Referring particularly to FIG. 8, an embodiment of the present invention is shown in which a series of time resolved image frames are acquired when a selected physiological event is occurring in the subject. In this case the physiological event is the phase of the subject's cardiac cycle that is indicated by a cardiac gating signal produced by an ECG monitor. First, as indicated at process block 300 a mask image is acquired prior to contrast injection. Time is not a critical factor at this point in the procedure and a complete, fully sampled, acquisition is performed at a selected cardiac phase following receipt of a cardiac gating signal.

After the mask image is acquired the contrast agent is injected as indicated at process block 302. A loop is then entered in which a series of frame images are acquired as the contrast agent flows into the region of interest. One cardiac gated image frame is acquired as indicted at process block 304 at the same cardiac phase as the mask image. With the multi-source system of FIG. 7, for example, the complete image frame may be acquired in a single 8 msec acquisition and then the sources 102 are rotated to another, interleaved position as indicated at process block 306. When the last image frame has been acquired as indicated at decision block 308, the acquisition phase of the procedure is completed and image reconstruction begins.

Prior to reconstructing the temporally resolved image frames a high resolution composite image is reconstructed as indicated at process block 310. This is a conventional filtered backprojection reconstruction using the interleaved projections in all of the acquired image frames. Since the image frames are acquired at interleaved view angles, collectively they provide a complete sampling of k-space and an artifact-free composite image can be produced using a conventional image reconstruction method. Since the composite image is to be used to reconstruct each image frame, the composite image is "edited" by subtracting the pre-contrast mask image from it to remove stationary tissues as indicated at process block 312. In addition, to provide a sparse data set for the highly constrained image reconstruction procedure to follow, the individual projection views in each acquired image frame has the corresponding projection view from the mask image subtracted from it.

The series of time resolved image frames are then reconstructed and displayed. A loop is entered in which the limited set of views that comprise an image frame are backprojected using the highly constrained backprojection method of the present invention as indicated at process block 314. As will be described in more detail below with reference to FIG. 9, each image frame is processed as indicated at 316 until the last image frame is reconstructed as determined at decision block 318. The reconstructed image frames may then be displayed as indicated at process block 320. The user may play the entire image frame sequence to observe the inflow of contrast agent into the vasculature of interest or the user may select one or more of the image frames that exhibit the best diagnostic information.

Successive image frames may also be combined to improve image SNR and when 3D image frames are produced, 2D MIP projection images are usually produced from them.

In the embodiment described above the composite image is formed using sets of interleaved projections acquired during the dynamic phase of the scan. All of the sets of acquired projections may be used in forming the composite image, and when the dynamic phase of the scan extends over a longer period of time, this may include one or more sets of projections acquired at the same projection angles. In such case the corresponding values in repeated projection views are averaged to improve SNR.

Figure 10:
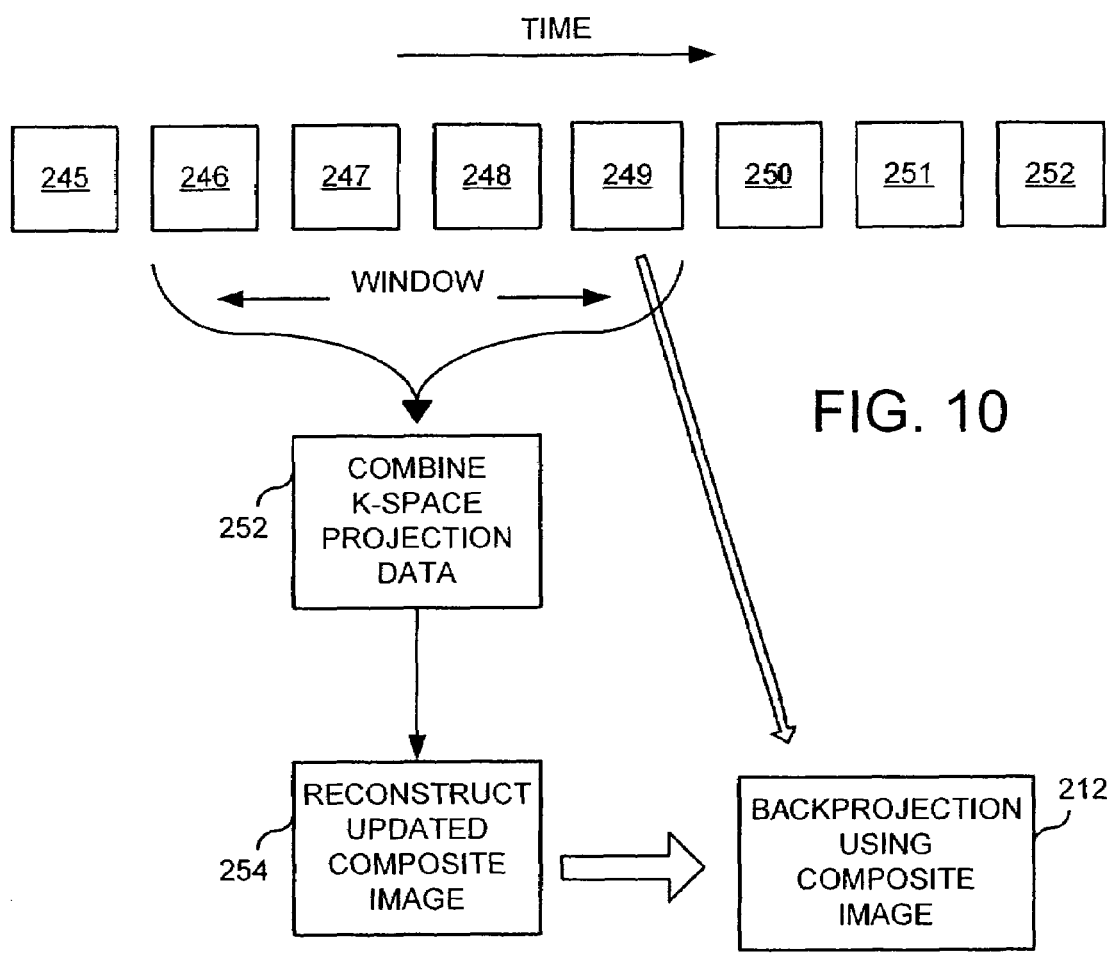
FIG. 10 is a pictorial representation of the method used to provide an up-to-date composite image.

On the other hand, there are also clinical applications where less than all the acquired sets of interleaved projections are used to reconstruct the composite image. For example, when a contrast agent is employed the subject looks considerably different at different times during the dynamic study. To reflect this change in the subject, more than one composite image may be reconstructed using less than all of the sets of acquired projections so that the composite image is kept up-to-date with the changing subject. This variation of the CTA scan is illustrated in FIG. 10 where the blocks 245-252 indicate successive image frame acquisitions that occur during the dynamic study. If the next image frame to be reconstructed is indicated by block 249, an updated composite image may be formed by combining the n=3 previously acquired image frames with the current image frame. More specifically, the interleaved k-space projection views for the n previous image frames and the current image frame are combined as indicated at process block 252 and an updated composite image is reconstructed from just these sets of projections as indicated at process block 254. During the subsequent highly constrained backprojection of image frame 249, the updated composite image is employed as indicated at process block 212.

Referring still to FIG. 10, the updated composite image is thus formed by a window of n previously acquired image frames and the current image frame, which most accurately reflect the current state of the subject being examined. When changes occur relatively slowly in the subject, n can be increased to include more previously acquired image frames. This improves the quality of the resulting updated composite image. On the other hand, when changes in the subject occur quickly, n may be reduced to as few as n=1 image frames in order to properly reflect the true state of the subject being imaged. There is thus a trade-off between high SNR on the one hand and more accurate depiction of dynamic changes on the other hand that results from the selection of n.

If the frame images are reconstructed after the dynamic scan is completed, the window of acquired image frames used to update the composite image may extend to include image frames acquired after the current image frame. For example, the image frame being reconstructed may be centered in the window with a substantially equal number of other image frames acquired before and after the current image frame. Or, the current image frame may be acquired at the beginning of the window. In this post-processing of the acquired image frames a number of different image frames can be reconstructed in which both the window size and the positioning of the window relative to the current image frame may be varied to achieve the best results.

Figure 11:
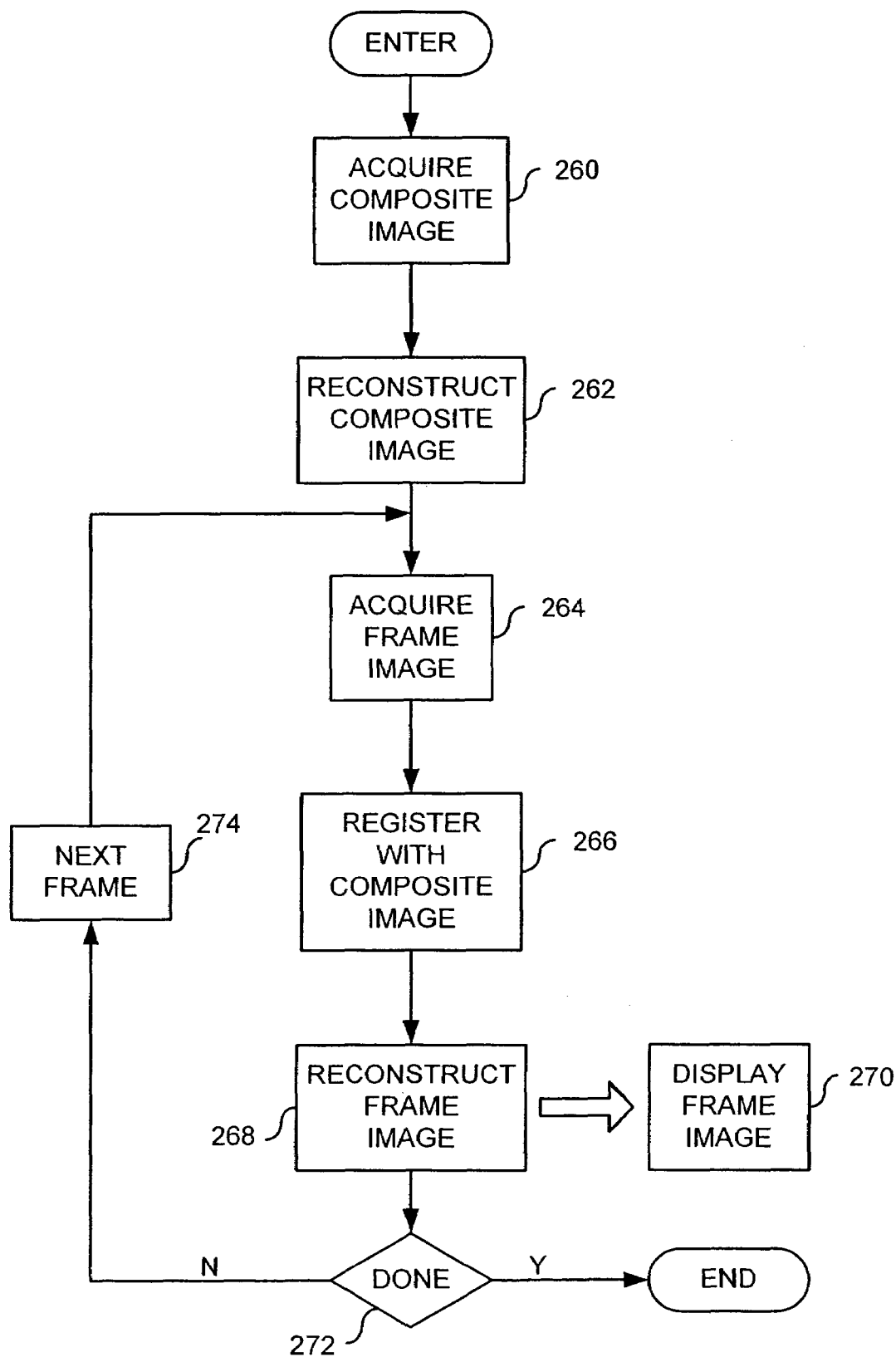
FIG. 11 is a flow chart of another preferred method for practicing the present invention.

There are also clinical applications where the composite image may be reconstructed from projections that are acquired prior to the dynamic acquisition phase of the scan. This is illustrated in FIG. 11 where a high resolution and high SNR composite image is acquired at the beginning of the procedure as indicated at process block 260 and reconstructed using a conventional filtered backprojection method as indicated at process block 262. A loop is then entered in which image frames are acquired and displayed as rapidly as possible.

An image frame is acquired as indicated at process block 264 with a minimal number of projection views as described above. As indicated at process block 266, these projections are aligned, or registered with the composite image to measure translational and rotational motion of the subject. This motion information is used to move the composite image such that it is aligned with the current position of the subject and then the image frame is reconstructed using the registered composite image in the highly constrained backprojection method as indicated at process block 268. The frame image may be displayed as indicated at process block 270 and the system branches at decision block 272 to acquire the next frame image as indicated at process block 274. It can be appreciated that if the CT system of FIG. 7 which acquires a frame image in 8 msecs is employed to practice this embodiment of the invention, frame images can be produced at a rate of up to 125 frames per second depending on the compute power used to provide near real time images of the subject.

Figure 9:
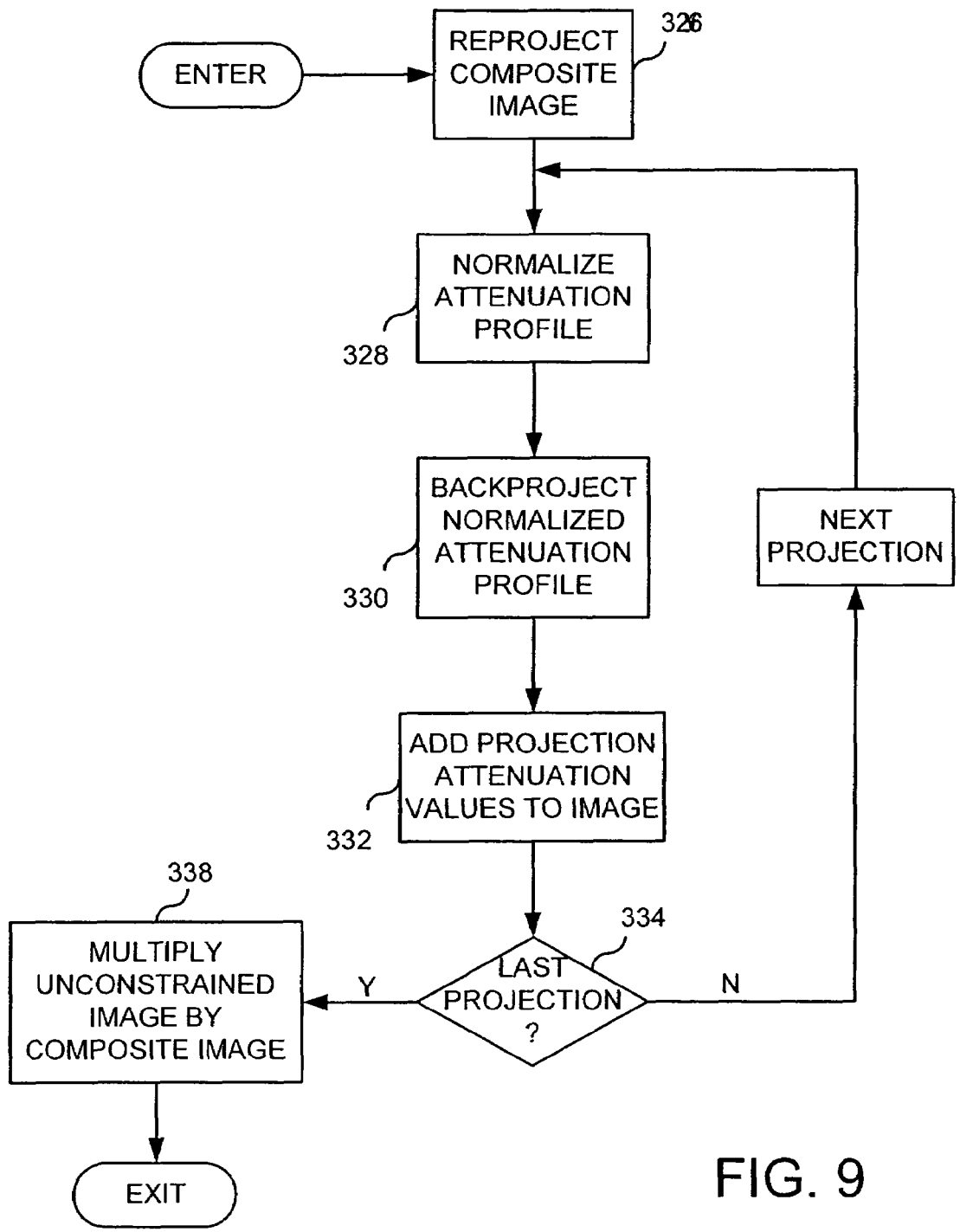
FIG. 9 is a flow chart of the frame image reconstruction method which forms part of the method of FIG. 8.
Figure 15:
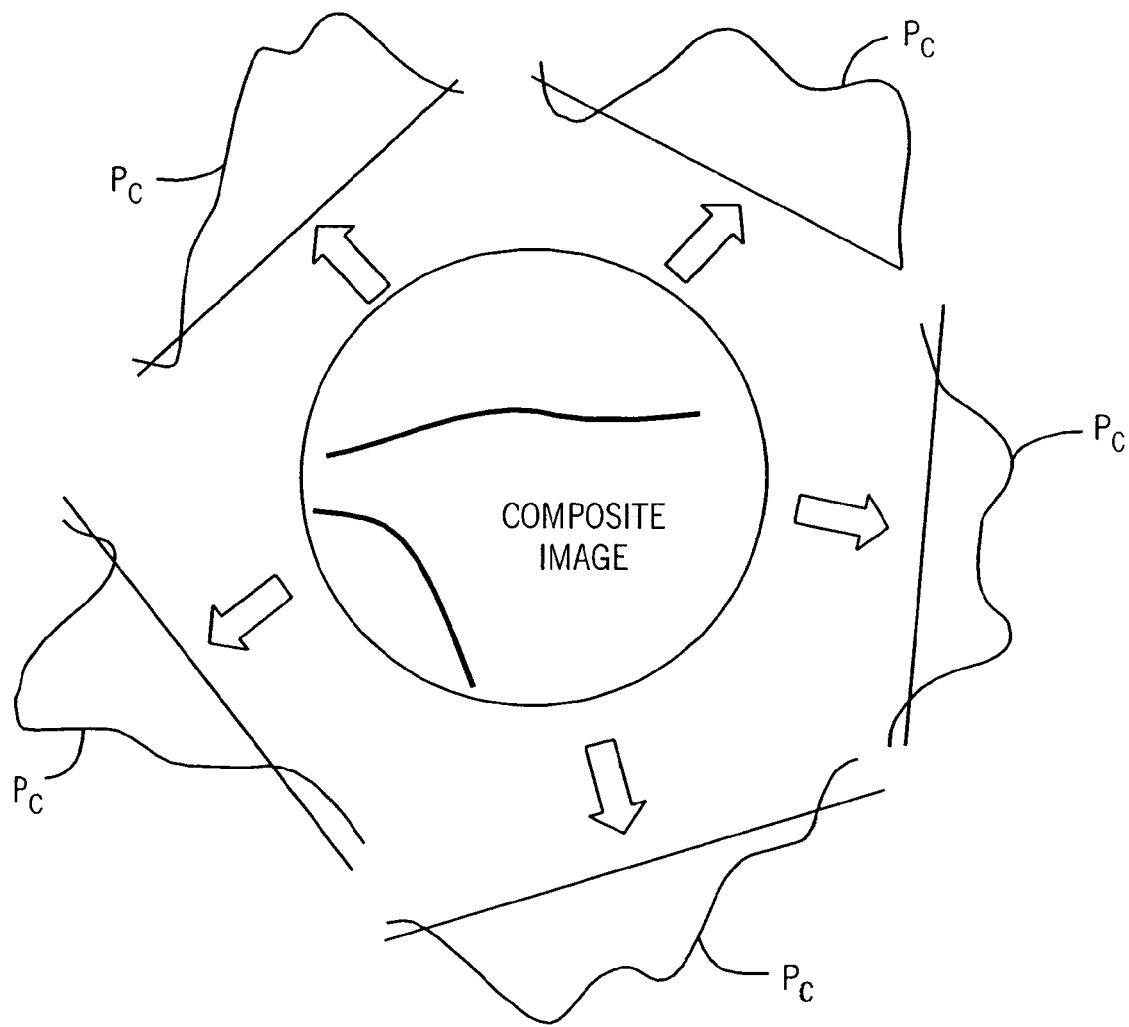
FIG. 15 is a pictorial representation of a composite image reprojection step used to practice one method for practicing the present invention.

Referring particularly to FIG. 9, the image frames are reconstructed in all of the above-described embodiments using the highly constrained backprojection method of the present invention. While there are a number of different ways to reconstruct an image frame using the present invention, in the preferred embodiment normalization is performed before the weighted backprojection. As indicated at process block 326 and illustrated in FIG. 15, for every attenuation profile P in the current image frame a corresponding composite image attenuation profile $P_c$ is calculated at the same view angle. This reprojection of the composite image is a Radon transformation such as that disclosed in "Computed Tomography Principles, Design, Artifacts, and Recent Advances," Jiang Hsich SPIE Press, 2003, Chapter 3.

A loop is then entered in which each image frame attenuation profile is normalized at process block 328, backprojected at process block 330 and summed with an unconstrained image frame at process block 332. More specifically, an image frame attenuation profile is normalized by dividing each attenuation ray sum P by the corresponding attenuation ray sum $P_c$ in the composite image reprojection at the same view angle. This normalized attenuation profile is then backprojected in the customary manner, but without any filtering. The resulting unconstrained image values are summed with those back projected from the other attenuation profiles for the current image frame.

When the last attenuation profile has been processed for the current image frame as determined at decision block 334, the reconstructed unconstrained image frame is constrained using the composite image as indicated at process block 338. This is a conventional matrix multiplication in which pixels in the unconstrained image frame are multiplied by the value of corresponding pixels in the composite image. In contrast to prior image reconstruction methods, far fewer projections are needed when the reconstruction method of the present invention is used, and thus, an image frame can be produced very quickly. Image artifacts due to undersampling are suppressed and the higher SNR of the composite image is conveyed to the reconstructed image frame.

It should be apparent that the present invention can be used with many different types of x-ray CT systems and in many different clinical applications. The invention is particularly advantageous where image frames must be produced quickly, with minimum projection data. In some applications the composite image may be acquired separately with high resolution and SNR, whereas in other applications the composite image may be formed from projections acquired during the time critical, dynamic phase of the scan.

A clinical application in which x-ray dose can be a significant issue is perfusion imaging. In this clinical procedure a mask image is acquired and then a contrast agent is administered to the subject. As the contrast agent flows into the tissues of interest (e.g., tissues in the region of a tumor or arterial blockage) a series of images are acquired from which parameters related to tissue health can be calculated. In a typical scan using conventional image reconstruction methods, 400 projection views may be acquired for the mask image and each of the 20 to 50 image frames acquired as the contrast flows into the tissues. This is a significant x-ray exposure and is considered excessive for many pediatric applications.

A perfusion study according to the present invention using either of the systems disclosed in FIG. 1 or 3 is depicted in FIG. 12. Initial rotations are performed to acquire a pre-injection mask as indicated at process block 400. This mask image is acquired at full x-ray dose. After the pre-injection mask data is obtained, a contrast agent is administered as indicated at process block 402. The contrast agent can be injected through typical arterial injection, but is preferably introduced intravenously, thereby reducing the invasiveness and discomfort of the procedure for the patient.

As indicated at process block 404 a series of image frames are then acquired at a low dose. In the first preferred embodiment this is achieved by rotating the gantry and acquiring a reduced number of projection views during the revolution. For example, whereas 400 projection views might be acquired during a normal scan, only 40 projection views are acquired during this low-dose acquisition. As determined at decision block 408, this is repeated as indicated at process block 306 until all of the desired image frames are acquired. However, whereas 40 views may be acquired for each image frame, they are different views. More specifically, the projection views acquired for each image frame are equally spaced and interleaved with the projection views acquired for the other image frames.

Each image frame in this embodiment is comprised of a reduced number of projection views (e.g., 40 views). As a result, the x-ray dose which the subject receives is only one-tenth the x-ray dose that would be received if a fully sampled image (e.g., 400 views) were acquired for each image frame.

In a second approach to the problem each image frame is acquired as a full set of 400 projection views. However, in this approach a lower x-ray dose is delivered to the subject by reducing the intensity of the x-ray beam produced by the x-ray source. This is usually achieved by reducing the x-ray tube current. Of course, by reducing the x-ray beam strength in this manner one would expect the SNR of the resulting reconstructed image to be reduced by a corresponding amount. By performing a highly constrained backprojection as described below, however, the lost SNR is recaptured.

After the image frames are acquired using either of the above-described low dose methods, the acquired mask projection views are subtracted as indicated at process block 410. This is a subtraction from attenuation values in each acquired image frame projection view of corresponding attenuation values in the mask image projection acquired at the same view angle. The resulting image frame projection views indicate the difference in x-ray attenuation caused by perfusion of the contrast agent into the tissues being examined.

Prior to reconstructing the perfusion images a high resolution composite image is reconstructed as indicated at process block 412. This is a conventional filtered backprojection reconstruction using the difference projection views from all of the acquired image frames. Since the image frames are acquired at interleaved view angles in the first embodiment, collectively they provide a complete sampling of Radon space and an artifact-free, high SNR composite image can be produced with a standard reconstruction method. In the second approach described above the corresponding low-dose views acquired for each image frame are averaged to provide a higher SNR composite image than would otherwise be produced from one complete set of low dose views.

The series of time resolved perfusion image frames are then reconstructed and displayed. A loop is entered in which the limited set of difference views that comprise an image frame are backprojected using the highly constrained method described above and shown in FIG. 9 as indicated at process block 414. Each perfusion image frame is reconstructed as indicated at 416 until the last perfusion image frame is reconstructed as determined at decision block 418. The reconstructed perfusion image frames may then be displayed as indicated at process block 420 or further processed to provide images indicative of tissue health.

By using the highly constrained image reconstruction method of the present invention the high SNR of the composite image is conveyed to each reconstructed image frame. Each image frame may thus be acquired with significantly lower x-ray dose to the patient. In this particular embodiment the total x-ray dose is reduced to almost one-tenth that of prior perfusion imaging methods.

Spiral computed tomography (CT) is a relatively new approach to CT that allows continuous data collection while a subject is advanced through the CT gantry. An x-ray source and detector are revolved around the subject as views are acquired at successive view angles and the subject is slowly moved axially through the gantry. This provides an uninterrupted volume of x-ray attenuation data. From this data, multiple contiguous or overlapping slices of arbitrary thickness can be reconstructed or a 3D image of a volume can be reconstructed. With spiral CT angiography (CTA), vascular structures can be selectively visualized by choosing an appropriate delay after IV injection of a contrast material. This gives excellent visualization of vessel lumina, stenoses, and lesions. The acquired data can then be displayed using 3D visualization techniques (e.g., volume-rendering, maximum intensity projection (MIP), and shaded surface display) to give an image of the vasculature. In contrast to conventional angiography, CTA is three-dimensional, thus giving the viewer more freedom to see the vasculature from different viewpoints.

One problem with spiral CTA is that the timing of table movement must be matched with the movement of the contrast bolus through the vasculature of interest. This "bolus chase" problem becomes more difficult when some vessels are "late filling" and the peak contrast enhancement is difficult to achieve.

A solution to this problem is to employ the present invention on a CT system which has multiple x-ray sources distributed along the axis of subject motion (z-axis) such that the entire 3D volume of interest can be continuously scanned during the in-flow of contrast agent. A CT system which provides this capability is illustrated in FIGS. 13A and 13B.

Figure 13A:
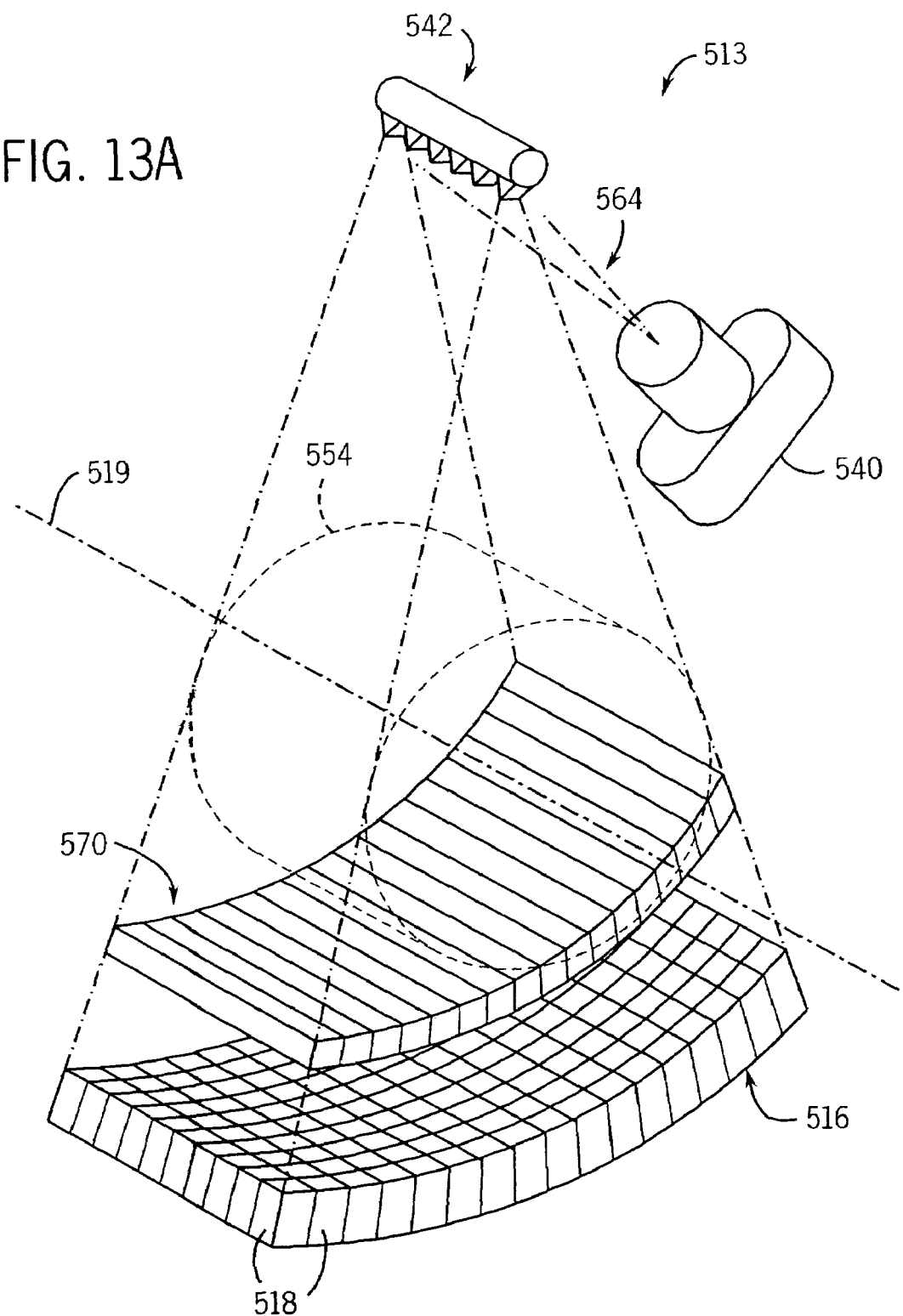
FIGS. 13A and 13B are pictorial representations of another CT apparatus that can be used to practice the present invention.
Figure 13B:
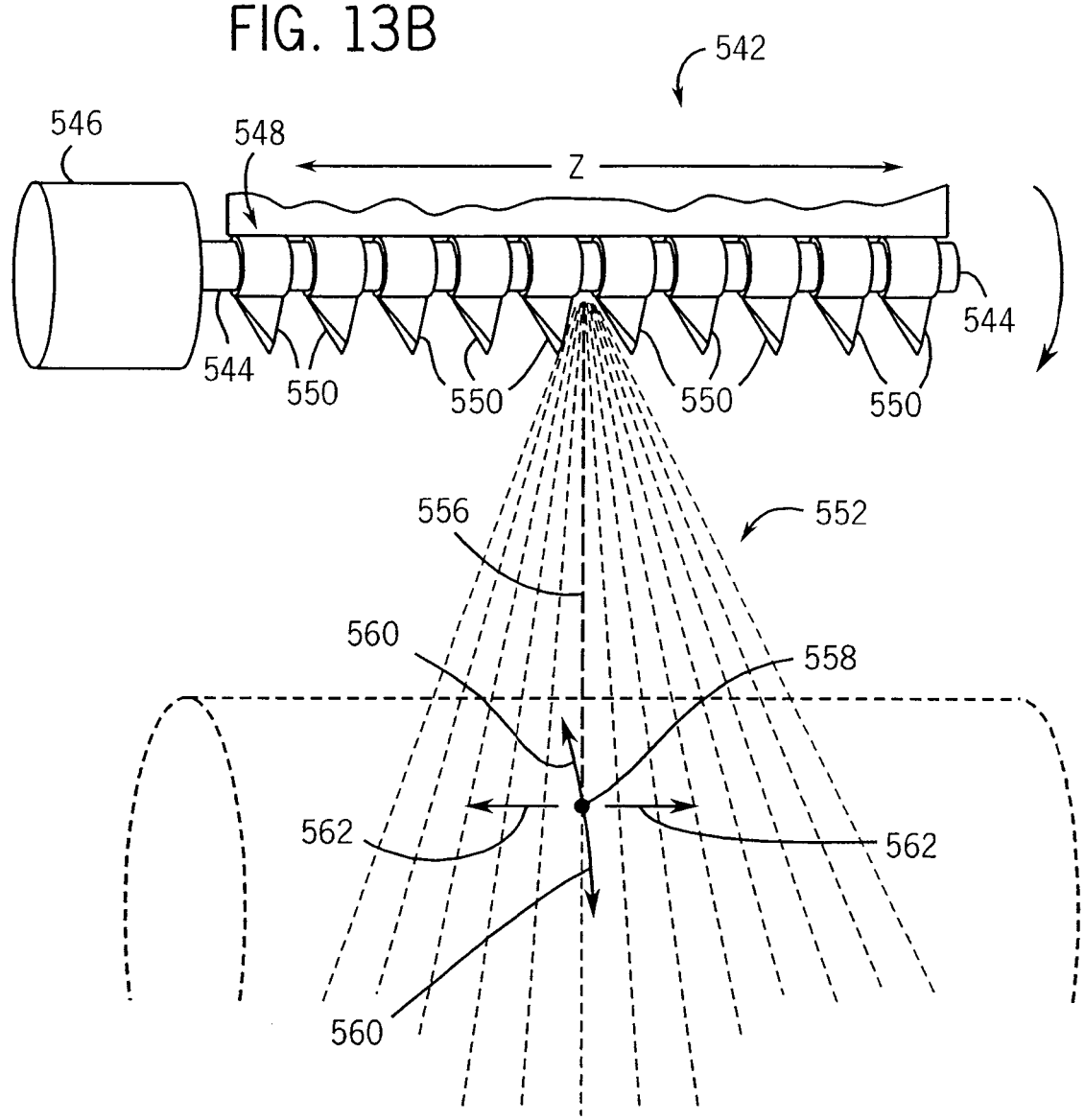
Figure 14:
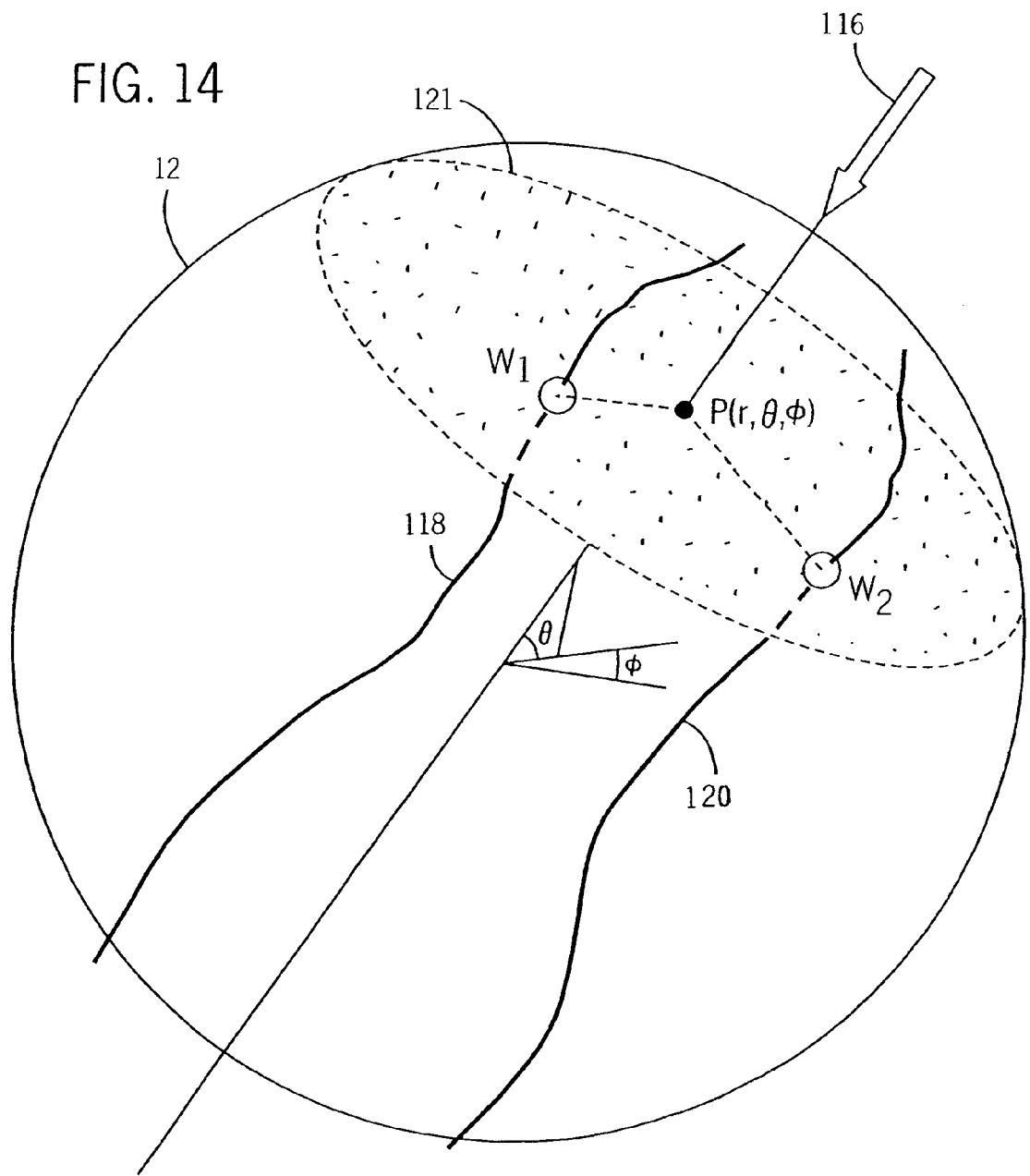
FIG. 14 is a pictorial representation of a 3D backprojection image reconstruction according to the present invention.

Referring particularly to FIG. 13A, the detector array 516 is a two-dimensional array of detector elements 518 arranged in rows and columns facing the x-ray source 513. The detector elements 518 may be conventional scintillation type x-ray detectors, but may also be ionization type or CZT detectors that are capable of at least a thirty frame per second readout rate. In the preferred embodiment the detector array extends along the z-axis 125 cm and it contains 2048 detector elements along the z-axis and 1024 elements in the gantry rotation direction.

Opposite the detector array 516 is the x-ray source 513, which in this preferred embodiment is comprised of an electron gun 540 and an anode assembly 542. As shown best in FIG. 13B, the anode assembly is comprised of a cylindrical anode 544 made of a high-Z material such as tungsten which is mounted for rotation by a motor 546. For coronary applications the anode 544 has a length of 30 cm and it is aligned substantially parallel to the z-axis 519 that extends through the center of the gantry.

Mounted adjacent the rotating anode 544 is a stationary, pre-patient collimator 548. The collimator 548 is constructed of a metal which shields x-rays and includes downward extending, wedge-shaped lobes 550 that are spaced equidistantly along the length of the anode 544. Anode segments are exposed between the lobes 550 and when an electron beam strikes one of the anode segments, a cone beam of x-rays 552 is produced and extends between the adjacent collimator lobes 550 and into a cylindrical FOV 554. The electron beam can be moved quickly to strike any of the exposed anode segments, and the cone beam 552 can thus be moved electronically along the z-axis to different locations. The anode assembly 542 is also rotated around the FOV 554 as the gantry rotates. The cone beam 552 which it produces can thus intersect the FOV 554 at any view angle. As shown in FIG. 13B, if the central ray of the cone beam 552 is represented by dashed line 556 and the intersection of this central ray with the cylindrical ROI surface is a scan point 558, a scan of the FOV 554 can be defined by the path of the scan point 558. In other words, a scan pattern of the FOV 554 is defined by movement of the scan point 558 circumferentially around the cylindrical FOV 554 as indicated by arrows 560 and its movement along the axial, z-axis as indicated by arrows 562.

Referring again to FIG. 13A, the anode assembly 542 and the electron gun 540 are enclosed in an airtight housing (not shown) that is evacuated. The electron gun 540 is positioned such that an electron beam 564 from the gun 540 strikes the anode assembly 542 to produce an x-ray cone beam directed toward the FOV 554. The electron gun 540 includes an electron source (not shown), for example, a heated filament, to produce electrons that are formed into an electron beam 564 and drawn toward the anode assembly 542 by an accelerating voltage maintained between the anode assembly 542 and the electron gun 540. Electrostatic plates or magnetic yokes (not shown) within the electron gun 540 deflect the electron beam 564 and enable it to be electronically steered to any location along the length of the anode assembly 542. The electron beam 564 can thus be quickly steered to impact any one of the anode segments disposed along its z-axis extent. This deflection provides almost instantaneous z-axis movement of the x-ray cone beam focal point and the only limitation on the rate at which the cone beam focal point is moved to different anode segments along the z-axis is the need to dwell long enough at any one segment to enable sufficient x-rays to be produced for the detector elements 518 that are used. Detector elements used in currently available CT scanners can acquire separate attenuation measurements at a rate of thirty per second, but it is anticipated that his measurement rate will increase substantially in the coming years. A 912266 element detector array that reads 900 frames per second is described, for example, by Saito et al, "Large Area 2D Detector For 3D CT 4DCT" *Medical Imaging* 2001: Physics of Medical Imaging, Proceedings of the SPIE Vol. 4320 (2001).

While a single electron gun 540 is used in the preferred embodiment, it should be apparent to those skilled in the art that separate electron guns may be used for each z-axis anode segment in the anode assembly 542. Rather than steering a single electron beam to scan along the z-axis, in this alternative embodiment the separate electron beams are switched on an off as prescribed to move the x-ray cone beam focal point along the z-axis.

Referring still to FIG. 13A, to shield the detector array 516 from external radiation and to thereby reduce the total x-ray dose needed to provide the desired SNR, a collimator 570 is disposed between the FOV 554 and the detector array 516. The collimator grid 570 is comprised of a set of spaced metal walls that extend along the z-axis and are aligned with the boundaries between adjacent detector elements 518. These walls absorb radiation that enters from external sources and blocks this radiation from striking the detector elements 518. The objective is to admit x-rays from the x-ray source 513 while blocking random radiation. In addition to reducing the required x-ray dose for an image of prescribed SNR, the reduced x-ray exposure means that the cone beam can be scanned along the z-axis at a higher rate.

To apply the present invention to a CTA scan using the multi-source scanner of FIGS. 13A and 13B the FOV 554 is divided into regions. There is one region for each cone beam x-ray source disposed along the z-axis 519. As will be described below, a separate composite image is reconstructed for each region and the image frames are reconstructed using these composite images on a region-by-region basis.

Figure 16:
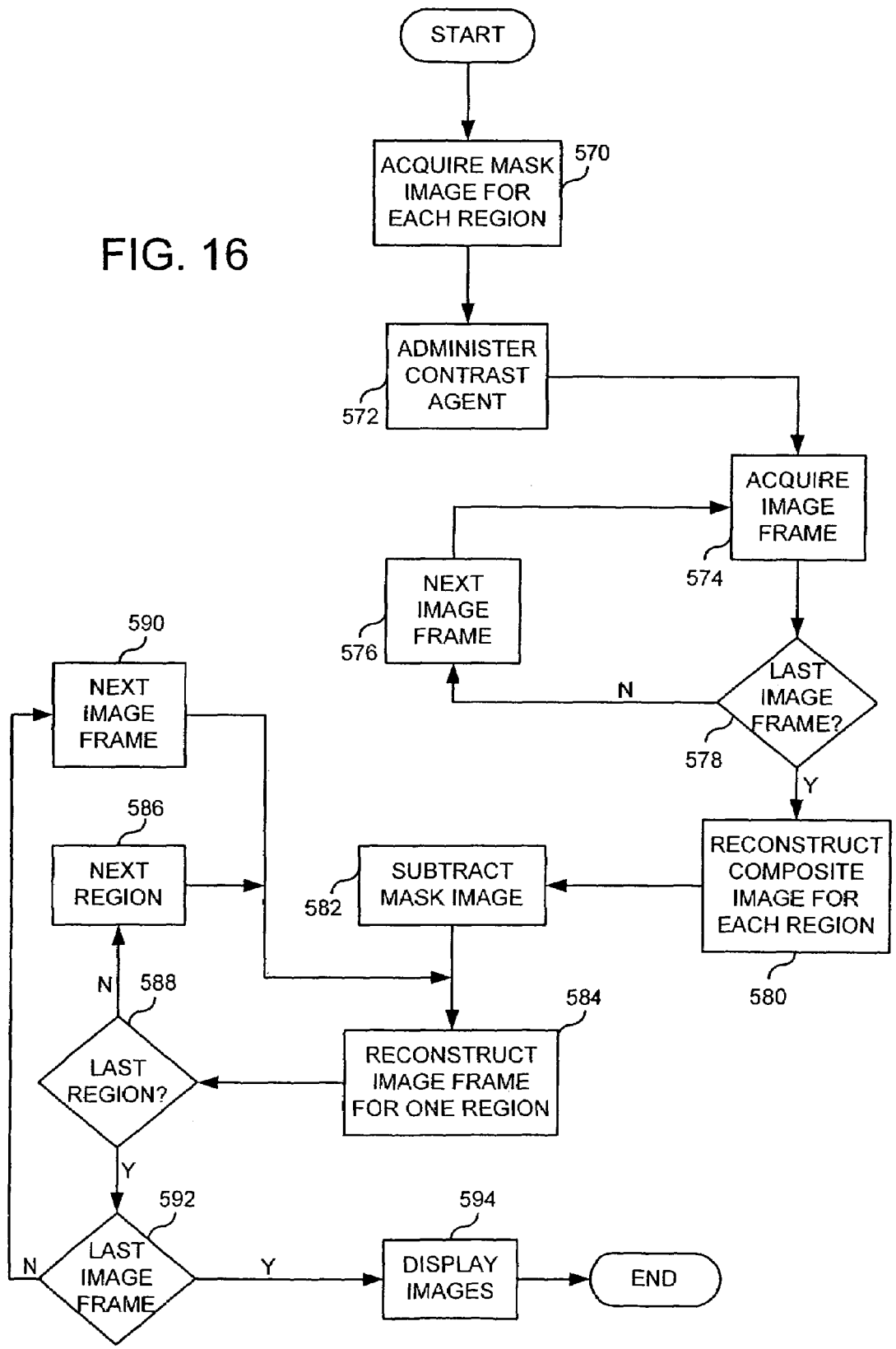
FIG. 16 is a flow chart of another method for practicing the present invention with the CT apparatus of FIG. 13.

Referring particularly to FIG. 16, the first step in a CTA scan using the structure of FIGS. 13A and B is to acquire a mask image as indicated at process block 570. This is a complete scan of the FOV 554 comprised of 300 or more views acquired by each x-ray source. A 3D mask image is reconstructed for each region using a conventional cone beam reconstruction method such as that described in chapter 3 in the above book by Jiang Hsieh.

The contrast agent is then administered as indicated at process block 572 and a loop is entered in which a series of image frames is acquired as the contrast agent flows through the vasculature in the FOV 554. More specifically, the gantry is revolved and an image frame is acquired as indicated at process block 574 for each x-ray source position. This is a highly undersampled acquisition with 30 equally spaced view angles acquired for each x-ray cone beam x-ray source over a gantry range of 180 degrees. Because each source is energized at a slightly different time, the acquired cone beam data for each x-ray source is kept separate even though the detector array 516 is a single assembly. Additional image frames are acquired as indicated at process block 576 until the scan is completed as determined at decision block 578. However, each additional image frame is acquired at different view angles which are interleaved with the view angles of the other acquired image frames. As a result, at the completion of the scan each cone beam x-ray source has acquired a fully sampled cone beam data set for its respective region.

As indicated at process block 580 a composite image for each region is reconstructed using all the views acquired during the scan. Because each region is fully sampled as described above, a conventional cone beam image reconstruction method is used as with the mask image reconstruction discussed above. As indicated at process block 582, the region mask images are then subtracted from the corresponding region composite image. In addition, to provide a more sparse data set, the projection views in the acquired mask are subtracted from the corresponding projection views in the acquired image frames.

The image frame reconstruction is performed next. As indicated at process block 584, one image frame for one region is reconstructed using the highly constrained reconstruction method described above and shown in FIG. 9. This is a three-dimensional constrained backprojection of the limited number of views acquired by one x-ray source during an image frame acquisition using the corresponding region composite image. Although the number of focal spot positions used to form each time frame is small, this is compensated by the large number of ray paths emanating from each focal spot position. For reconstruction of a 3D volume of sparse angiographic or perfusion data good results can be obtained with about 300 focal spot positions. R. Boutchko, G. H. Chen, C. A. Mistratta, J. Hsieh, S. K. Patch, and R. Senzig, Z-Scan: "Feasibility Study of an Ultra-Fast Volume CT Scanner", Fully 3D meeting, St. Malo, May 2003

The image frame for each region is reconstructed as indicated at process block 586, and when the last region has been processed as determined at decision block 588, the next image frame is reconstructed as indicated at process block 590. The three-dimensional region image frames may be merged to form one image frame of the entire FOV 554. When the last image frame is reconstructed as determined at decision block 592, the merged image frames are stored and displayed as indicated at process block 594.

There are other clinical applications to which the present invention may also be applied. For example, the determination of coronary flow reserve involves the acquisition of two series of image frames, one before administration of a vasodilating substance such as dipyridamole and the other immediately after administration of the vasodilator. The first time series of cardiac images is acquired after acquisition of a mask image and the injection of a contrast agent. These cardiac image frames are acquired at a reduced dose during the first pass of the contrast flow through the heart. The vasodilator is administered and a second series of low dose cardiac image frames is acquired after injection of a contrast agent. A composite image is reconstructed from the first series of interleaved cardiac image frames and it is used to reconstruct each cardiac image frame in the first series according to the highly constrained backprojection method of the present invention. A second composite image is then reconstructed from the low dose cardiac image frames in the second series. This second composite image is used to reconstruct each cardiac image frame in the second series according to the highly constrained backprojection method of the present invention. Parametric images reflecting mean transit time (MTT) and vascular blood volume are calculated from each series of reconstructed coronary image frames and these are combined to provide parametric images of blood flow both before and after administration of the vasodilator. The ratio of the blood flow before and after vasodilation is an indication of coronary flow reserve at each image pixel and the associated vascular bed. As with the perfusion examination described above, this flow reserve image can be acquired at nearly one-tenth of the x-ray dose normally required to produce a clinically acceptable image.

What is claimed is:
1. A method for producing an image of a subject positioned in the field of view (FOV) of a computed tomography (CT) system, the steps comprising:
   a) acquiring with the CT system a set of projection views of the subject positioned in the FOV;

b) producing a composite image with the CT system which indicates an attenuation value at each composite image pixel of the subject positioned in the FOV; and c) reconstructing an image of the subject by:
   c)i) backprojecting each projection view in the set into the FOV and weighting the value backprojected into each image pixel by the attenuation value of the corresponding pixel in the composite image; and
   c)ii) summing the backprojected values for each image pixel to produce the image.

2. The method as recited in claim 1 in which each image pixel backprojected value $\mu_n$ is calculated in step c)i) as $$\mu_n = (P \times C_n) \Big/ \sum_{n=1}^{N} C_n$$

where: P=the projection view value being backprojected;
$C_n$=corresponding pixel attenuation value in the composite image;
$\mu_n$=the attenuation value of the $n^{th}$ pixel along the backprojection path; and
N=total number of pixels along the backprojection path.

3. The method as recited in claim 1 in which step b) includes editing the composite image to remove an object therein and to thereby substantially reduce the appearance of that object in the reconstructed image.

4. The method as recited in claim 1 in which the weighting step c)i) includes normalizing each projection view using a corresponding projection view from the composite image and multiplying the backprojected value by the corresponding pixel in the composite image.

5. The method as recited in claim 1 which further includes:
   d) repeating steps a) and c) to reconstruct a series of images that depict the subject during an examination; and
   e) periodically updating the composite image during the reconstruction of the series of images to depict therein changes that occur in the subject during the examination.

6. The method as recited in claim 5 in which the updating of the composite image includes reconstructing the composite image using projection views acquired in step a).

7. The method as recited in claim 1 in Which the composite image is produced by acquiring data with the CT system in response to a gating signal indicative of a selected physiological event in the subject, and step a) is performed in response to a gating signal indicative of the selected physiological event.

8. The method as recited in claim 7 in which the selected physiological event is cardiac phase of the subject's heart.

9. The method as recited in claim 1 in which steps a) and c) are repeated to acquire a plurality of sets of projection views and reconstruct a corresponding plurality of images in which each set of projection views acquired in step a) are interleaved with the projection views in other sets of acquired projection views and the composite image is produced by combining sets of interleaved projection views acquired in step a).

10. The method as recited in claim 1 which includes detecting the location of the subject when performing step a) and registering the composite image with the detected subject location.

11. The method as recited in claim 1 in which the FOV is three-dimensional, a three-dimensional image is produced, and the image $I_{(x,y,z)}$ reconstructed in step c) is:

$$I(x,y,z) = \Sigma(P(r,\theta,\phi) * C(x,y,z)_{(r,\theta,\phi)} / P_c(r;\theta,\phi))$$

where the summation ($\Sigma$) is over all projection views in the acquired set;
$I_{(x,y,z)}$ is the image value at FOV pixel location x,y,z; $P_{(r,\theta,\phi)}$ is the back projected value from the view acquired at a view angle $\theta$, $\phi$; $C_{(x,y,z)}$ is the composite image value at the pixel location x,y,z; and $P_c(r,\theta,\phi)$ is the profile value projected from the composite image at the view angle $\theta$, $\phi$.

12. The method as recited in claim 1 which includes:
   d) acquiring a mask image that depicts at each of its image pixels the subject positioned in the FOV prior to the administration of a contrast agent;
   e) administering a contrast agent to the subject prior to performing steps a) and b); and
   f) subtracting the mask image from the composite image prior to performing step c).

13. The method as recited in claim 12 in which both the mask image and the composite image are acquired as sets of projection views and step f) is performed by subtracting projection views in the mask image set from corresponding projection views in the composite image set.

14. The method as recited in claim 12 in which step f) is performed by subtracting pixels in the mask image from corresponding pixels in the composite image.

15. The method as recited in claim 1 which includes:
   d) acquiring a mask image as a set of projection views;
   e) administering a contrast agent to the subject prior to performing steps a) and b); and
   f) subtracting from each projection view in the set a corresponding projection view acquired in step d) before performing step c).

16. The method as recited in claim 15 which includes:
   g) subtracting the mask image from the composite image prior to performing step c).

17. The method as recited in claim 1 which further includes:
   d) repeating steps a) and c) to reconstruct a series of image frames that depict the subject during an examination; and
   e) registering the composite image with each set of image frame projection views prior to performing step c).

18. The method as recited in claim 1 which includes:
   d) reprojecting the composite image at view angles used to perform step a); and
   in which the weighting in step c)i) includes normalizing each projection view by dividing values therein by corresponding values in the projection view of the composite image at the same view angle.

19. A method for producing an image of a subject positioned in the field of view (FOV) of a computed tomography (CT) system, the steps comprising:
   a) acquiring with the CT system a set of projection views of the subject positioned in the FOV;
   b) repeating step a) to acquire additional sets of projection views, wherein the sets of acquired projection views are interleaved with each other;
   c) reconstructing a composite image from acquired projection views which indicates an attenuation value at each composite image pixel of the subject positioned in the FOV; and
   d) reconstructing a frame image of the subject by:
      d)i) normalizing each projection view in one of said sets of projection views;
      d)ii) backprojecting each normalized projection view into the FOV;
      d)iii) summing the backprojected pixel values for the set of projection views; and d)iv) multiplying the summed pixel values by the corresponding pixel value in the composite image.

20. The method as recited in claim 19 in which steps c) and d) are repeated to produce additional frame images, wherein the acquired projection views used to reconstruct the composite image in step c) are updated to reflect changes occurring over time in the subject.

21. The method as recited in claim 19 which includes acquiring and reconstructing a mask image of the subject; injecting a contrast agent into the subject prior to performing step a); and subtracting the mask image from the composite image produced in step c).

22. A method for producing an image of a subject positioned in the field of view (FOV) of a computed tomography (CT) system having a plurality of x-ray sources disposed along an axis of rotation, the steps comprising:
   a) acquiring a plurality of image frames with each x-ray source, each image frame including a set of projection views of the subject and the projection views in each set being interleaved with the projection views in the other sets;
   b) reconstructing a region composite image for each x-ray source from interleaved projection views in a plurality of said sets of projection views;
   c) reconstructing an image frame for one region using the projection views corresponding to that region and the composite image for that region which includes:
      c)i) normalizing each projection view corresponding to that region;
      c)ii) backprojection each normalized projection view into the region of the FOV;
      c)iii) summing backprojected values produced in step c)ii) at each pixel in the region; and
      c)iv) weighting the backprojected values with corresponding pixel values in the composite image for the region:
   d) repeating step c) to reconstruct additional region image frames; and
   e) combining the region image frames to produce the image frame.

23. The method as recited in claim 22 in which includes:
   acquiring a mask image for each region;
   administering a contrast agent to the subject prior to performing step a); and
   step b) includes subtracting from each region composite image the corresponding region mask image.

24. A method for producing a plurality of image frames of a subject in the field of view (FOV) of a computed tomography (CT) system the steps comprising:
   a) acquiring a plurality of image frames, each image frame including a set of projection views of the subject;
   b) reconstructing a composite image by combining the projection views from the acquired image frames; and
   c) reconstructing each image frame by
      c)i) normalizing each image frame projection view using information derived from the composite image;
      c)ii) backprojecting each normalized projection view;
      c)iii) summing the backprojected values; and
      c)iv) weighting the backprojected values with the values in the composite image at corresponding locations in the FOV.

25. The method as recited in claim 24 in which each image frame is comprised of projection views that under sample Radon space, the projection views in each acquired image frame are interleaved with the projection views in other acquired image frames, and the composite image is reconstructed in step b) by using substantially all the interleaved projection views.

26. The method as recited in claim 24 in which each image frame is comprised of projection views acquired with an x-ray beam intensity that is substantially less than the x-ray beam intensity used to acquired an image frame of comparable quality and the composite image is reconstructed in step b) by averaging substantially all the projection views acquired at the same view angle.

27. A method for acquiring perfusion images of tissues positioned in the field of view (FOV) of a computed tomography (CT) system, the steps comprising:
   a) acquiring a fully sampled, mask image of the tissues with the CT system;
   b) administering a contrast agent;
   c) acquiring a series of low dose image frames of the tissues with the CT system;
   d) subtracting mask image projection views acquired in step a) from image frame projection views acquired in step c) to produce difference image frame projection views;
   e) combining difference image frame projection views from a plurality of said image frames and reconstructing a composite image therefrom; and
   f) reconstructing perfusion images by:
   f)i) backprojecting each difference image frame projection view from an acquired image frame into the FOV and weighting the value backprojected into each image pixel by the value of a corresponding pixel in the composite image; and
   f)ii) summing the backprojected values for each image pixel.

28. The method as recited in claim 27 in which each image pixel backprojected value $\mu_n$ is calculated in step f)i) as $$\mu_n = (P \times C_n) \bigg/ \sum_{n=1}^{N} C_n$$

where: P=the projection view value being backprojected;
   $C_n$=corresponding pixel attenuation value in the composite image;
   $\mu_n$=the attenuation value of the $n^{th}$ pixel along the backprojection path; and
   N=total number of pixels along the backprojection path.

29. The method as recited in claim 27 in which the weighting in step f)i) includes normalizing each image frame difference projection view using a corresponding projection view from the composite image and multiplying the backprojected value by the corresponding pixel in the composite image.

30. The method as recited in claim 27 in which step c) is performed by acquiring each image frame as an undersampled set of projection views which are interleaved with the projection views acquired for the other image frames.

31. The method as recited in claim 30 which in step e) is performed by combining into a data set image frame difference projection views acquired at different view angles and reconstructing the composite image using the combined data set.

32. The method as recited in claim 30 in which step e) is performed by averaging image frame difference projection views acquired at the same view angles and reconstructing the composite image using the averaged image frame difference projection views.

33. The method as recited in claim 27 in which step c) is performed by acquiring each image frame with an x-ray beam intensity that is substantially less than the x-ray beam intensity used to acquired an image frame of comparable quality.

34. A method for producing an image of a subject positioned in the field of view (FOV) of a computed tomography (CT) system, the steps comprising:
 a) acquiring with a CT system a composite image of the subject;
 b) acquiring with the CT system a set of projection views of the subject;
 c) measuring the motion of the subject with respect to the composite image using projection views acquired in step b);
 d) registering the composite image with the current subject position using the motion measured in step c); and
 e) reconstructing a frame image of the subject by:
  e)i) backprojecting each projection view in the set into the FOV and weighting the value backprojected into each image pixel by the value of a corresponding pixel in the registered composite image; and
  e)ii) summing the backprojected values for each image pixel to produce the frame image.

35. The method as recited in claim 34 in which the weighting step e)i) includes normalizing each projection view using a corresponding projection view of the registered composite image and multiplying the backprojected value by the corresponding pixel in the registered composite image.

* * * * *